(12) United States Patent
Walsh

(10) Patent No.: US 8,100,253 B2
(45) Date of Patent: Jan. 24, 2012

(54) METHODS AND APPARATUSES FOR TRANSFERRING DISCRETE ARTICLES BETWEEN CARRIERS

(75) Inventor: Bradley Edward Walsh, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 389 days.

(21) Appl. No.: 12/494,632

(22) Filed: Jun. 30, 2009

(65) Prior Publication Data

US 2010/0326796 A1    Dec. 30, 2010

(51) Int. Cl.
*B65G 29/00* (2006.01)

(52) U.S. Cl. .............. 198/476.1; 198/377.08; 198/415; 198/471.1

(58) Field of Classification Search ............. 198/377.04, 198/377.08, 408, 415, 459.8, 476.1, 699.1, 198/792, 803.5
See application file for complete search history.

(56) References Cited

U.S. PATENT DOCUMENTS

| | | | |
|---|---|---|---|
| 3,963,557 A | 6/1976 | Pattereson | |
| 4,181,555 A | 1/1980 | Hoffmann | |
| 4,255,777 A * | 3/1981 | Kelly | ............ 361/228 |
| 4,297,157 A | 10/1981 | Van Vliet | |
| 4,333,790 A | 6/1982 | Schaffron | |
| 4,429,781 A | 2/1984 | Holzhauser | |
| 4,574,022 A | 3/1986 | Johnson et al. | |
| 4,578,133 A | 3/1986 | Oshefsky et al. | |
| 4,610,751 A | 9/1986 | Eschler | |
| 4,632,721 A | 12/1986 | Hoffmann et al. | |
| 4,726,876 A | 2/1988 | Tomsovic, Jr. | |
| 4,758,293 A | 7/1988 | Samida | |
| 4,767,487 A | 8/1988 | Tomsovic, Jr. | |
| 4,786,046 A | 11/1988 | Freeman et al. | |
| 4,838,982 A | 6/1989 | Klaeser et al. | |
| 4,880,102 A | 11/1989 | Indrebo | |
| 4,921,387 A | 5/1990 | Bennington | |
| 4,925,520 A | 5/1990 | Beaudoin et al. | |
| 4,960,186 A | 10/1990 | Honda | |
| 5,025,910 A | 6/1991 | Lasure et al. | |

(Continued)

FOREIGN PATENT DOCUMENTS

AT    104442 B    10/1926

(Continued)

OTHER PUBLICATIONS

PCT International Search Report dated Mar. 17, 2011, 15 pages.

*Primary Examiner* — Douglas Hess
(74) *Attorney, Agent, or Firm* — Charles R. Matson

(57) ABSTRACT

An apparatus for transferring an article from a first carrier moving at a first speed to a second carrier moving at a second speed is provided. The apparatus comprises a support member comprising a track comprising an arcuate portion, and a carrier member configured to be moved relative to the track. The carrier member comprises a surface configured to receive the article from the first carrier in a receiving zone and deposit the article onto the second carrier in an application zone, an aperture in the surface, and a passage in fluid communication with the aperture. The apparatus further comprises a vacuum manifold in fluid communication with the passage. The carrier member is configured to be moved relative to the vacuum manifold. The apparatus also comprises a linear motor operably engaged with the carrier member and configured to move the carrier member relative to the track.

20 Claims, 14 Drawing Sheets

U.S. PATENT DOCUMENTS

| | | | |
|---|---|---|---|
| 5,091,039 A | 2/1992 | Ujimoto et al. |
| 5,116,452 A | 5/1992 | Eder |
| 5,149,392 A | 9/1992 | Plaessmann |
| 5,177,841 A | 1/1993 | Hamuro et al. |
| 5,224,405 A | 7/1993 | Pohjola |
| 5,235,515 A | 8/1993 | Ungpiyakul et al. |
| 5,305,653 A | 4/1994 | Ohtani et al. |
| 5,380,381 A | 1/1995 | Otruba |
| 5,400,574 A * | 3/1995 | Spatafora | 53/531 |
| 5,413,651 A | 5/1995 | Otruba |
| 5,429,694 A | 7/1995 | Herrmann |
| 5,447,219 A * | 9/1995 | Dworak et al. | 198/377.04 |
| 5,518,106 A * | 5/1996 | Allard | 198/459.5 |
| 5,556,504 A | 9/1996 | Rajala et al. |
| 5,584,954 A | 12/1996 | van der Klugt et al. |
| 5,591,297 A | 1/1997 | Ahr |
| 5,643,396 A | 7/1997 | Rajala et al. |
| 5,684,344 A | 11/1997 | Takei |
| 5,693,195 A | 12/1997 | Saito et al. |
| 5,695,963 A | 12/1997 | McKnight et al. |
| 5,709,770 A | 1/1998 | Asghar et al. |
| 5,716,478 A | 2/1998 | Boothe et al. |
| 5,735,996 A | 4/1998 | Asghar et al. |
| 5,759,340 A | 6/1998 | Boothe et al. |
| 5,766,406 A | 6/1998 | Bohn et al. |
| 5,776,289 A | 7/1998 | Steidinger |
| 5,783,032 A | 7/1998 | O'Callaghan et al. |
| 5,837,087 A | 11/1998 | Ahr |
| 5,849,143 A | 12/1998 | Ingalls |
| 5,850,711 A | 12/1998 | Takahashi |
| 5,888,343 A | 3/1999 | Olson |
| 5,895,555 A | 4/1999 | Van Den Bergh |
| 5,927,473 A * | 7/1999 | Draghetti | 198/474.1 |
| 5,932,039 A | 8/1999 | Popp et al. |
| 5,965,963 A | 10/1999 | Chitayat |
| 5,994,798 A | 11/1999 | Chitayat |
| 6,022,443 A | 2/2000 | Rajala et al. |
| 6,059,710 A | 5/2000 | Rajala et al. |
| 6,074,333 A | 6/2000 | Rajala et al. |
| 6,086,694 A | 7/2000 | Winter et al. |
| 6,139,004 A | 10/2000 | Couillard et al. |
| 6,149,755 A | 11/2000 | McNichols et al. |
| 6,165,306 A | 12/2000 | Rajala |
| 6,170,636 B1 | 1/2001 | Een et al. |
| 6,319,347 B1 | 11/2001 | Rajala et al. |
| 6,325,201 B1 | 12/2001 | Bailey et al. |
| 6,350,070 B1 | 2/2002 | Tasma |
| 6,422,375 B1 | 7/2002 | Hellman et al. |
| 6,431,241 B1 | 8/2002 | Gonzalo |
| 6,450,321 B1 | 9/2002 | Blumenthal et al. |
| 6,544,375 B1 | 4/2003 | Schmitz |
| 6,550,517 B1 | 4/2003 | Hilt et al. |
| 6,604,623 B2 | 8/2003 | Sumi et al. |
| 6,692,196 B1 | 2/2004 | Simm et al. |
| 6,705,453 B2 | 3/2004 | Blumenthal et al. |
| 6,722,494 B2 | 4/2004 | Nakakado |
| 6,732,498 B2 * | 5/2004 | Keen et al. | 53/567 |
| 6,748,996 B2 | 6/2004 | Nakakado et al. |
| 6,766,217 B1 | 7/2004 | Hamada |
| 6,766,843 B2 | 7/2004 | Hilt et al. |
| 6,811,019 B2 | 11/2004 | Christian et al. |
| 6,814,217 B2 | 11/2004 | Blumenthal et al. |
| 6,820,671 B2 | 11/2004 | Calvert |
| 6,848,566 B2 | 2/2005 | Harnish et al. |
| 6,866,137 B2 | 3/2005 | Ohiro et al. |
| 6,899,780 B2 | 5/2005 | Rajala et al. |
| 6,918,485 B2 | 7/2005 | Holston et al. |
| 6,942,086 B2 * | 9/2005 | Bridges et al. | 198/377.08 |
| 7,093,705 B2 | 8/2006 | Ohiro et al. |
| 7,134,258 B2 | 11/2006 | Kalany et al. |
| 7,278,203 B2 | 10/2007 | Aoyama et al. |
| 7,341,087 B2 | 3/2008 | Tabor et al. |
| 7,398,870 B2 | 7/2008 | McCabe |
| 7,530,444 B2 * | 5/2009 | Draghetti et al. | 198/474.1 |
| 7,533,709 B2 | 5/2009 | Meyer |
| 7,587,966 B2 | 9/2009 | Nakakado et al. |
| 7,643,904 B2 | 1/2010 | Aoyama et al. |
| 7,721,872 B2 | 5/2010 | Aoyama et al. |
| 7,770,712 B2 | 8/2010 | McCabe |
| 2002/0023723 A1 | 2/2002 | Blumenthal et al. |
| 2003/0010603 A1 | 1/2003 | Corrigan |
| 2003/0079330 A1 | 5/2003 | Stopher et al. |
| 2004/0089516 A1 | 5/2004 | Christian et al. |
| 2004/0245069 A1 | 12/2004 | Hook et al. |
| 2004/0262127 A1 | 12/2004 | Harnish et al. |
| 2006/0185135 A1 | 8/2006 | Yamamoto et al. |
| 2007/0227858 A1 | 10/2007 | Aoyama et al. |
| 2008/0023296 A1 | 1/2008 | Aoyama et al. |
| 2008/0196564 A1 | 8/2008 | McCabe |
| 2008/0276439 A1 | 11/2008 | Andrews et al. |
| 2009/0312739 A1 | 12/2009 | Umebayahi et al. |
| 2010/0012458 A1 | 1/2010 | Guiliani et al. |
| 2010/0258240 A1 | 10/2010 | McCabe et al. |
| 2010/0270126 A1 | 10/2010 | Piantoni et al. |
| 2010/0300838 A1 | 12/2010 | McCabe |

FOREIGN PATENT DOCUMENTS

| | | | |
|---|---|---|---|
| EP | 0812789 A2 | 12/1997 |
| EP | 1772403 A1 | 4/2007 |
| EP | 1303240 B1 | 8/2008 |
| WO | WO 01/53156 A1 | 7/2001 |
| WO | WO 02/07664 A2 | 1/2002 |
| WO | WO 2005/035414 A1 | 4/2005 |

* cited by examiner

METHODS AND APPARATUSES FOR TRANSFERRING DISCRETE ARTICLES BETWEEN CARRIERS

FIELD OF THE INVENTION

The present disclosure relates to methods and apparatuses for transferring discrete articles between carriers and, more particularly, relates to methods and apparatuses for transferring one or more discrete articles from a first carrier moving at a first speed to a second carrier moving at a second speed that is different than the first speed.

BACKGROUND OF THE INVENTION

Absorbent articles, such as diapers, for example, are manufactured by a process where discrete parts, articles, and/or components, such as leg elastic, waist elastic, labels, tapes, and/or other fasteners (referred to together as "articles"), for example, are applied to a moving carrier web comprised of an absorbent material. Often, a speed at which the articles are fed into the process is not the same as a speed of the moving carrier web itself. Thus, the speed of the articles must be changed to match the speed of the moving carrier web to properly apply the articles to the carrier web without adversely affecting the process or a finished product produced by the process. In view of the importance of matching the speed of the articles to the speed of the moving carrier web, this technology should be improved.

SUMMARY OF THE INVENTION

In one non-limiting embodiment, the present disclosure is directed, in part, to an apparatus for transferring one or more articles from a first carrier moving at a first speed to a second carrier moving at a second speed that is different than the first speed. The apparatus comprises a support member comprising a vacuum manifold and an endless track defining an arcuate perimeter. The apparatus further comprises a carrier member movably engaged with the support member and movable with respect to the endless track. The carrier member comprises an outer surface configured to receive the one or more articles from the first carrier in a receiving zone and configured to deposit the one or more articles onto the second carrier in an application zone. The carrier member further comprises an aperture in the outer surface and a channel in fluid communication with the aperture and configured to be in fluid communication with the vacuum manifold. The apparatus further comprises a linear motor positioned at least on the support member. The linear motor is operably engaged with the carrier member and is configured to move the carrier member relative to the endless track. The linear motor is configured to move the outer surface of the carrier member at a third speed through the receiving zone and at a fourth speed through the application zone. The third speed is different than the fourth speed.

In another non-limiting embodiment, the present disclosure is directed, in part, to an apparatus for transferring an article from a first carrier moving at a first speed to a second carrier moving at a second speed that is different than the first speed. The apparatus comprises a support member comprising a track comprising an arcuate portion, and a carrier member configured to be moved relative to the track. The carrier member comprises a surface configured to receive the article from the first carrier in a receiving zone and deposit the article onto the second carrier in an application zone. The carrier member further comprises an aperture in the surface and a passage in fluid communication with the aperture. The apparatus further comprises a vacuum manifold in fluid communication with the passage. The carrier member is configured to be moved relative to the vacuum manifold. The apparatus also comprises a linear motor operably engaged with the carrier member and configured to move the carrier member relative to the track. The linear motor is configured to move the surface of the carrier member at a third speed through the receiving zone and at a fourth speed through the application zone. The third speed is different than the fourth speed.

In yet another non-limiting embodiment, the present disclosure is directed, in part, to a method of transferring an article from a first carrier moving at a first speed to a second carrier moving at a second speed. The method comprises the steps of providing a support member comprising an endless track comprising an arcuate perimeter. The method further comprises providing a carrier member movable relative to the support member. The carrier member comprises an outer surface and an aperture in the outer surface. The aperture is in fluid communication with a vacuum manifold. The method further comprises receiving an article from the first carrier onto the outer surface of the carrier member and holding the article on the outer surface of the carrier member with air passing through the aperture to the vacuum manifold. The method also comprises moving the carrier member with a linear motor such that the carrier member moves relative to the support member about the endless track to a position proximate to the second carrier. The linear motor comprises a permanent magnet on the carrier member and an electromagnet on the support member. The method further comprises cooling the electromagnet with air passing through the aperture to the vacuum manifold, and depositing the article from the carrier member onto the second carrier.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting embodiments of the disclosure taken in conjunction with the accompanying drawings.

DETAILED DESCRIPTION OF THE INVENTION

Figure 1:
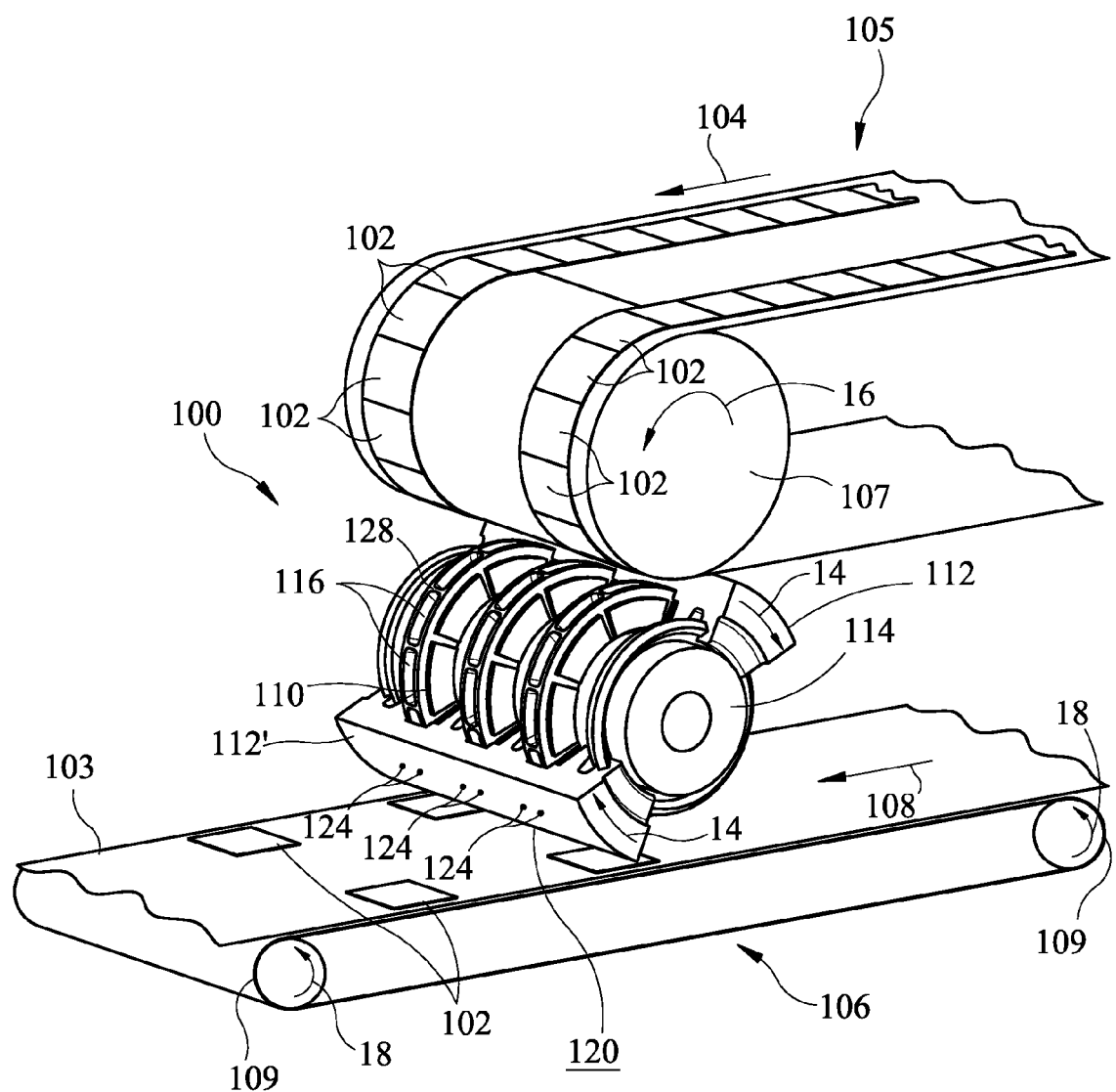
FIG. 1 is a perspective view of a system using an apparatus to transfer an article from a first carrier moving at a first speed to a second carrier moving at a second speed according to one non-limiting embodiment.

Various non-limiting embodiments of the present disclosure will now be described to provide an overall understanding of the principles of the structure, function, manufacture, and use of the apparatuses and methods disclosed herein. One or more examples of these non-limiting embodiments are illustrated in the accompanying drawings. It is to be appreciated that the apparatuses and methods specifically described herein and illustrated in the accompanying drawings are non-limiting example embodiments and that the scope of the various non-limiting embodiments of the present disclosure are defined solely by the claims. The features illustrated or described in connection with one non-limiting embodiment may be combined with the features of other non-limiting embodiments. Such modifications and variations are intended to be included within the scope of the present disclosure.

The present disclosure provides methods and apparatuses for receiving discrete articles, discrete components, and/or discrete articles, such as leg elastic, waist elastic, labels, tapes, and/or other fasteners (hereafter referred to generally as "article" or "articles"), for example, which are traveling at a first speed on a first carrier, and transferring the articles to a second carrier traveling at a second speed. The apparatuses and methods may be useful for transferring the articles from a first carrier to a continuously moving carrier web positioned on a second carrier and used in the manufacturing of absorbent articles, such as diapers, training diapers, pull-up pants, incontinence briefs, and undergarments, for example. The carrier web can comprise one or more absorbent materials. It is to be appreciated that the methods and apparatuses of the present disclosure may also be suitable for any other uses that require the transfer of an article or a component from a first carrier moving at a first speed to a second carrier moving at a second speed. These other uses can comprise various manufacturing processes in any industry.

Several methods for changing the speed of the articles, such that the articles can be applied to the continuously moving carrier web of material or substrate (hereafter referred to as a "carrier web"), are described below. One method is known as the slip cut or the cut and slip method. In this method, the material of the articles, which is traveling at a slower speed than the carrier web, is fed into a knife and anvil roll apparatus, wherein the anvil roll has a surface speed equal to the speed of the carrier web. As the material of the articles is fed into the knife and anvil roll apparatus, the material slips against the surface of the anvil roll until the knife cuts it into individual articles. The purpose of the "slip" is to ensure that the correct amount of the material is metered into the system at the desired tension prior to cutting by the knife. As the material is cut into discrete articles, a vacuum is activated in the anvil roll to hold the articles to an outer surface of the anvil roll without slipping, so that the articles are accelerated to the surface speed of the anvil roll. The anvil roll then carries each article to a predetermined release point along the anvil roll's rotational path whereupon the vacuum on the article is released, causing the article to disengage the anvil roll and to be received on the carrier web while the article and the carrier web are both traveling at the same speed. The main drawback of this method is that the coefficient of friction between the material to be cut and the anvil roll must be low enough such that, in conjunction with the holding force keeping the material and the surface of the anvil roll in contact, the total tension generated in the material to be cut is not great enough to generate significant elongation in the material to be cut. This elongation, if it occurs, can contribute to high variability in the final cut length and placement of the articles on the moving carrier web.

Another method creates festoons in the moving carrier web to reduce the speed of the carrier web to the speed of the material of the articles to be applied to the carrier web. As such, at least portions of the carrier web are temporarily slowed down to the speed of the material of the articles, with the excess portion of the carrier web gathering in festoons. The articles of the material are then applied to the carrier web while both the articles and the carrier web are traveling at the same speed. The festoons are then released to allow the portion of the moving carrier web to return to its original speed. This method has two main drawbacks. First, the carrier web must be festooned and then released, sometimes damaging or otherwise changing the properties of the carrier web. Second, this method requires a large amount of space in typical absorbent article production systems because there is a direct relationship between line speed and storage space needed for the festooned portions of the carrier web.

To improve the related systems discussed above, the present disclosure provides an apparatus that is configured to transfer articles from a first carrier moving at a first speed to a carrier web of absorbent material on a second carrier moving at a second speed. In one embodiment, referring to FIGS. 1 and 2, an apparatus 100 is configured to transfer articles 102 from a first carrier 105 moving at a first speed to a carrier web 103 on a second carrier 106 moving at a second speed. In various embodiments, the first speed may be faster than, the same as, or slower than the second speed. In one embodiment, the apparatus 100 may receive the articles 102 traveling at the first speed from the first carrier 105. In various embodiments, the articles 102 can be held to a surface of the first carrier 105 by friction, static electricity, by a low strength adhesive, and/or by a vacuum, for example. The first carrier 105 may travel in the direction indicated by arrow 104 of FIG. 1. In one embodiment, the first carrier 105 can be rotated partially about two or more drums or other suitable rotatable members. At least one of the drums can be driven by any suitable driving member, such as a motor, for example, such that the first carrier 105 can be driven or moved at a suitable speed about the two or more drums. As the articles 102 are conveyed by the first carrier 105 toward the apparatus 100, the articles 102 can be rotated partially about a drum 107 in a direction indicated by arrow 16. Once the one or more articles 102 travel partially around the circumference of the drum 107, they can be transferred to an outer surface 120 of carrier members 112 and 112' of the apparatus 100, as described in further detail below. In various embodiments, the articles 102 may be transferred from the first carrier 105 to the carrier members 112 and 112' in a number of arrangements, for example, referring to FIG. 1, two sets of the articles 102 are transferred from the first carrier 105 to the carrier members 112 and 112' during each full rotation of the carrier members 112 and 112'. The apparatus 100 can then accelerate the carrier members 112 and 112' and the articles 102 thereon for placement onto a carrier web 103 situated on a second carrier 106.

In one embodiment, referring again to FIGS. 1 and 2, the carrier web 103, like the articles 102 of the first carrier 105, can be engaged with a surface of the second carrier 106 by friction, by a low strength adhesive, by static electricity, and/or by a vacuum, for example. The second carrier 106, much like the first carrier 105, can be rotated about two or more drums 109 or other suitable rotatable members. The two or more drums 109 can be rotated in a direction indicated by arrows 18 to drive or move the carrier web 103 in the direction indicated by arrow 108 of FIG. 1. The carrier web 103 can comprise a web of absorbent articles, such as diapers, training diapers, pull-up pants, feminine hygiene products, incontinence briefs, and/or undergarments, for example. In one embodiment, the absorbent articles may be formed of a back sheet, a core, and a top sheet, for example. The back sheet may be formed of polyethylene and/or any other suitable material used in absorbent articles. The core may be formed of air felt, shredded cellulose fiber, and/or any other suitable material used in absorbent articles. The top sheet may be formed of polypropylene and/or any other suitable material used in absorbent articles.

Figure 2:
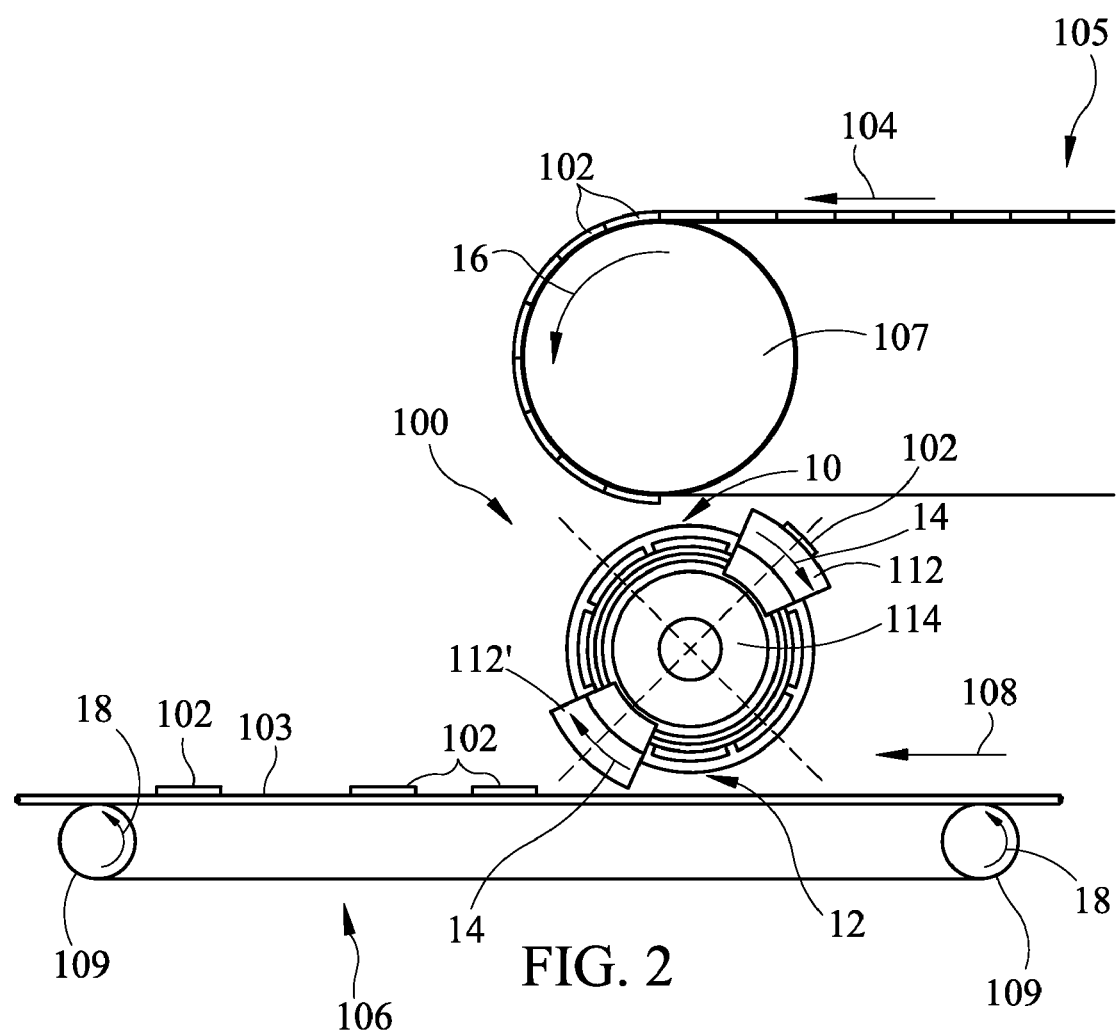
FIG. 2 is a side view of the system of FIG. 1 according to one non-limiting embodiment.

In one embodiment, still referring to FIGS. 1 and 2, the apparatus 100 can be positioned intermediate the first carrier 105 and the second carrier 106. As a result, each of the carrier members 112 and 112' of the apparatus 100 can receive the articles 102 from the first carrier 105 in a receiving zone 10, accelerate the speed of the articles 102 about a track formed on a support member 114 of the apparatus 100 to match a speed of the second carrier 106, and deposit the articles 102 onto the carrier web 103 positioned on the second carrier 106 in an application zone 12. In one embodiment, the carrier members 112 and/or 112' of the apparatus 100 can move relative to or about the track of the support member 114 in a rotational direction 14. While two carrier members 112 and 112' are illustrated in some example embodiments, it will be understood that one carrier member (see, e.g., FIG. 3) or another number of carrier members can be provided on the apparatus 100. It will also be understood that the support member 114 will be mounted at a position intermediate the first carrier 105 and the second carrier 106. In one embodiment, the support member 114 can be rigidly mounted to a support structure (not illustrated), for example.

Figure 4:
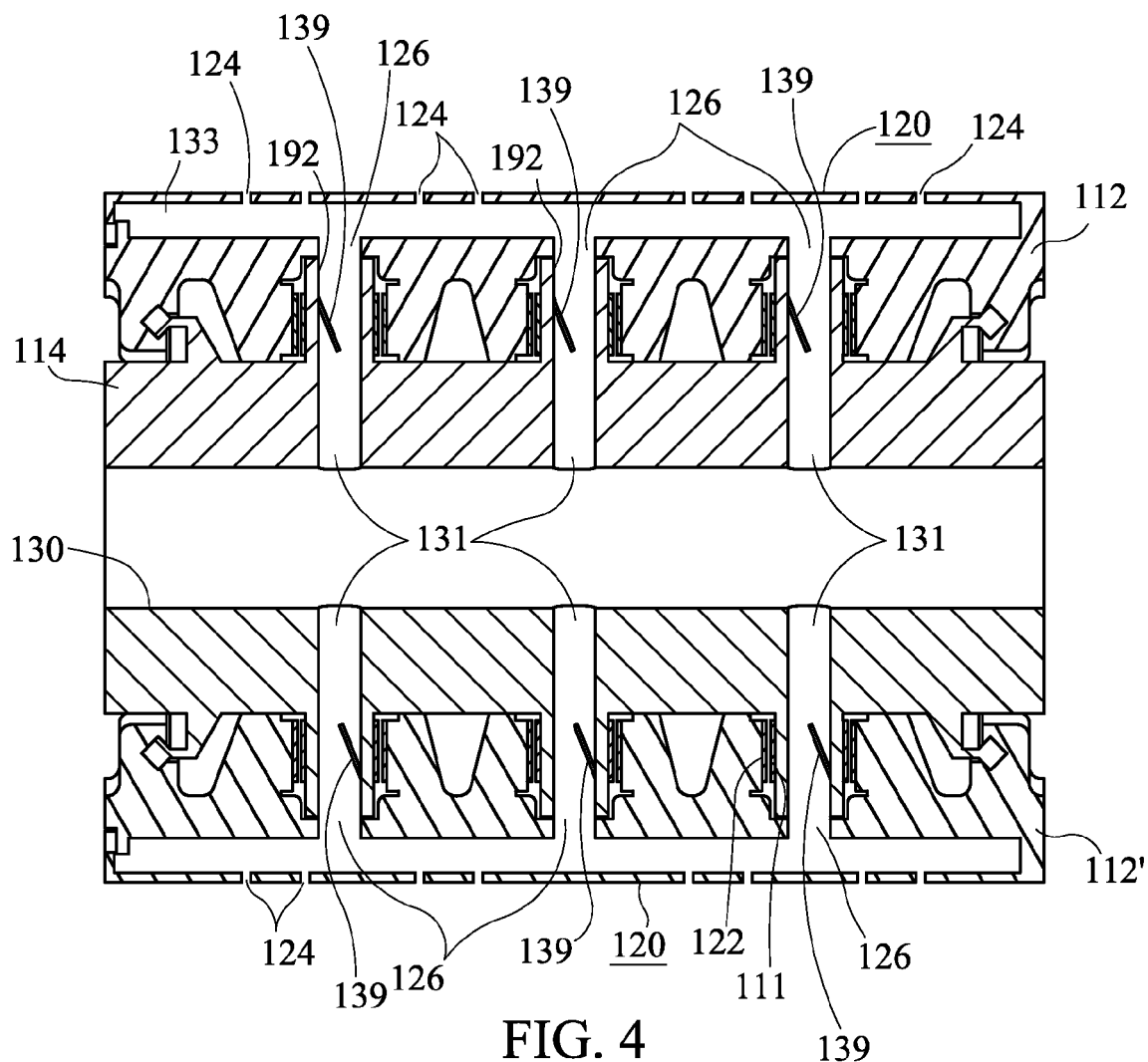
FIG. 4 is a cross sectional view of the apparatus of FIG. 1 according to one non-limiting embodiment.

In one embodiment, referring to FIGS. 1 and 4, the support member 114 can have an axially extending bore 130 defined therethrough. It will be appreciated that the axially extending bore 130 can be configured to receive a vacuum from a vacuum system comprising a vacuum pump or other suitable vacuum producing device. In various embodiments, the vacuum system may also comprise any associated vacuum lines, tubing, and/or any other suitable vacuum transfer mechanism in fluid communication with the axially extending bore 130. The axially extending bore 130 can be in fluid communication with one or more conduits 131 in the support member 114, such that vacuum conditions or conditions less than atmospheric pressure can be created within the conduits 131. In one embodiment, a seal can be provided within the conduits 131 to prevent, or at least inhibit, the vacuum conditions from extending through the conduits 131. The support member 114 can comprise one or more projections 128 extending therefrom. In one embodiment, a track can be defined between two projections 128 and the projections 128 can extend radially outward from the track. In one embodiment, the projections 128 can house a portion of the conduits 131. The conduits 131 and the axially extending bore 130 together can comprise a vacuum manifold 116.

Figure 3:
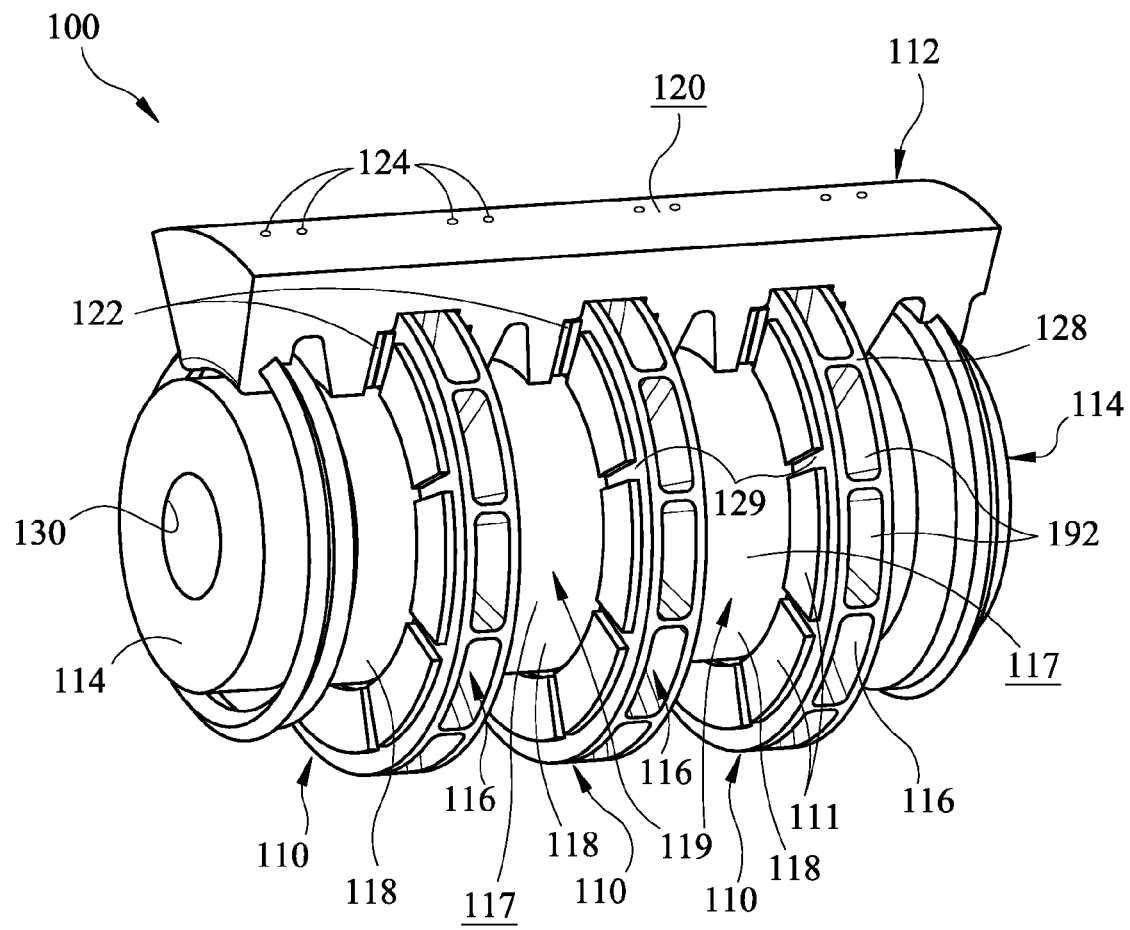
FIG. 3 is a perspective view of an apparatus according to one non-limiting embodiment.

As referenced above, referring to FIGS. 3 and 4, the support member 114 can further comprise a track 118, such as an endless track, for example, positioned about a perimeter, a circumference, or a portion of the support member 114 and extending in a direction perpendicular to, or transverse to, the axial direction of the axially extending bore 130. As illustrated in FIG. 3, a track 118 can be formed intermediate a first projection 128 and a second projection 128. In one embodiment, the track 118 may be defined in a space 119 above a surface 117 of the support member 114. In one embodiment, the track 118 can comprise an arcuate portion. In other embodiments, the track 118 can be circular, substantially circulate, ovate, substantially ovate, semi-circular, and/or substantially semi-circular, for example. It is to be appreciated, upon review of the present disclosure, that the track 118 can also comprise any other suitable shape. In one embodiment, a support member may comprise a track that may not be endless. In such an embodiment, a carrier member can reciprocate about the track between a receiving zone 10 and an application zone 12, for example.

In one embodiment, referring to FIG. 3, the carrier member 112 can be configured to be moved relative to or about the track 118 to transfer the articles 102 from the first carrier 105 to the second carrier 106. In various embodiments, the carrier members 112 and can be configured to rotate fully around the track 118, if the track is endless. In various embodiments, each carrier member 112 can comprise one or more channels or passages 126 configured to receive the vacuum from the vacuum manifold 116 and, more specifically, from the conduits 131, when the carrier member 112 is positioned over at least one of the conduits 131 (as it travels around the endless track 118). In one embodiment, three or more passages 126 can be provided along the length of the carrier member 112. These three passages 126 can be in fluid communication with three or more conduits 131 of the support member 114, for example. The one or more conduits 131 can be positioned along the length of the support member 114 and can also extend radially outward from side walls of the axially extending bore 130. The carrier member 112 can also define a void 133 in fluid communication with the one or more conduit 131. The void 133 can be positioned proximate to an outer surface 120 of the carrier member 112. The outer surface 120 can define one or more apertures 124 in fluid communication with the void 133. The apertures 124 may comprise one or more openings in the outer surface 120 of any suitable shape. Further, the apertures 124 may be arranged on the outer surface 120 in any suitable pattern for holding the articles 102 thereto. As such, vacuum conditions can be created within the void 133 and the apertures 124, when the one or more passages 126 are in fluid communication with one or more of the conduits 131. As a result, the articles 102 can be held to the outer surface 120 of the carrier member 112 proximate to or over at least one of the apertures 124 owing to the vacuum conditions created within the apertures 124. In such an embodiment, the articles 102 can be porous such that air can be drawn through the articles 102 and into the apertures 124 by the vacuum pump in fluid communication with the vacuum manifold 116. In one embodiment, instead of using the vacuum system, the articles 102 may be held to the outer surface 120 of the carrier member 112 using an adhesive, friction, static electricity, and/or any other suitable method of holding the articles 102 to the outer surface 120. In one embodiment, the one or more passages 126 may be configured to be in fluid communication with the vacuum manifold 116 and/or the one or more conduits 131 at a location intermediate the vacuum manifold and the carrier member 112. Of course, the one or more conduits 131 of the support member 114 which are not in fluid communication with the one or more passages 126 of the carrier member 112 (as the carrier member 112 rotates about the track 118) can be sealed such that the vacuum conditions can be created in the passages 126, the void 133, and the apertures 124 of the carrier member 112. In one embodiment, the void 133 can be eliminated and the passages 126 can be configured to be in direct fluid communication with the one or more apertures 124, for example.

In one embodiment, referring to FIG. 4, the vacuum manifold 116 and/or the one or more of the conduits 131 may comprise a seal 139 movable between a first, engaged position and a second, disengaged position. In one embodiment, the seal 139 may comprise a flapper-type seal, for example. The seal 139 may permit fluid communication between the one or more conduits 131 and the one or more passages 126 in the carrier member 112 or 112' when in the second, disengaged position and may at least partially seal the one or more conduits 131 from the one or more passages 126 when in the first, engaged position.

Figure 5:
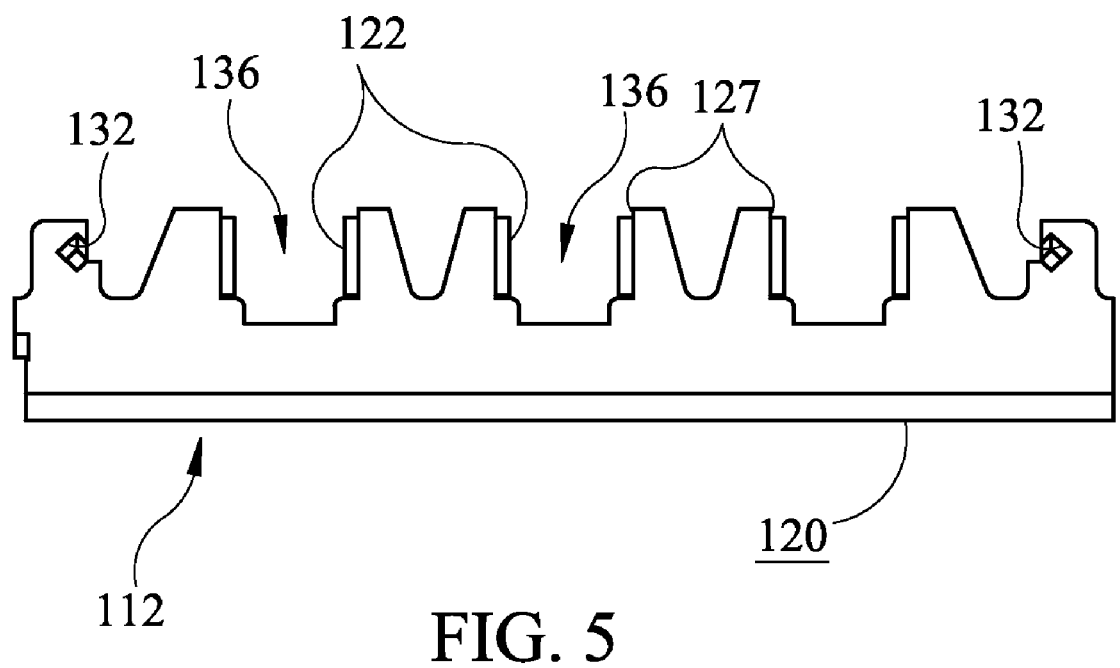
FIG. 5 is a front view of a carrier member of the apparatus of FIG. 3 according to one non-limiting embodiment.

In one embodiment, referring to FIGS. 3-5, a carrier member, such as the carrier member 112, for example, may comprise a plurality of receiving slots 136 along the length of the carrier member 112. The receiving slots 136 can be configured to be engaged with the projections 128 extending radially outward from the support member 114. In one embodiment, one or more magnets 122 can be positioned on each of or some of sidewalls 127 of the receiving slots 136. The magnets 122 can interact with one or more magnets 111 positioned on each or some of sidewalls 129 on the projections 128. Together, the magnets 122 and the magnets 111 can comprise a linear motor 110. In various embodiments, each receiving slot 136 may be configured to receive at least a portion of each of the projections 128, such that the magnets 111 and 122 can face each other. In one embodiment, the linear motor 110 may comprise one or more permanent magnets 122 positioned on side walls 127 of the receiving slots 136 of the carrier member 112 and one or more electromagnets 111 positioned on the sidewalls 129 of the projections 128, or vice versa. The permanent magnets 122 may not require wires for power or position feedback of the carrier member 112, while the electromagnets 111 may require wires for power and position feedback of the carrier member 112. In one embodiment, the one or more electromagnets 111 may be configured to be magnetically engaged with one or more permanent magnets 122, when the one or more electromagnets 111 are energized. In various embodiments, the side walls 129 of each projection 128 may each comprise a number of electromagnets 111, for example, such that at least one electromagnet 111 can be magnetically engaged with the carrier member 112, regardless of the position of the carrier member 112 about the endless track 118.

The permanent magnets 122 can comprise any known permanent magnets. In one embodiment, the permanent magnets 122 can each comprise a magnet formed from ferromagnetic materials, such as iron, nickel, cobalt, rare earth metals, and/or alloys of the above-mentioned metals, for example. The electromagnets 111 may each comprise a coil of wire which may act as a magnet when an electric current passes through the coil of wire, but may stop acting as a magnet when the electric current stops flowing through the coil of wire. The coil of wire may be wrapped around a core of ferromagnetic material, such as steel, for example, which may enhance the magnetic field produced by the coil and, therefore, by the electromagnet.

Figure 8:
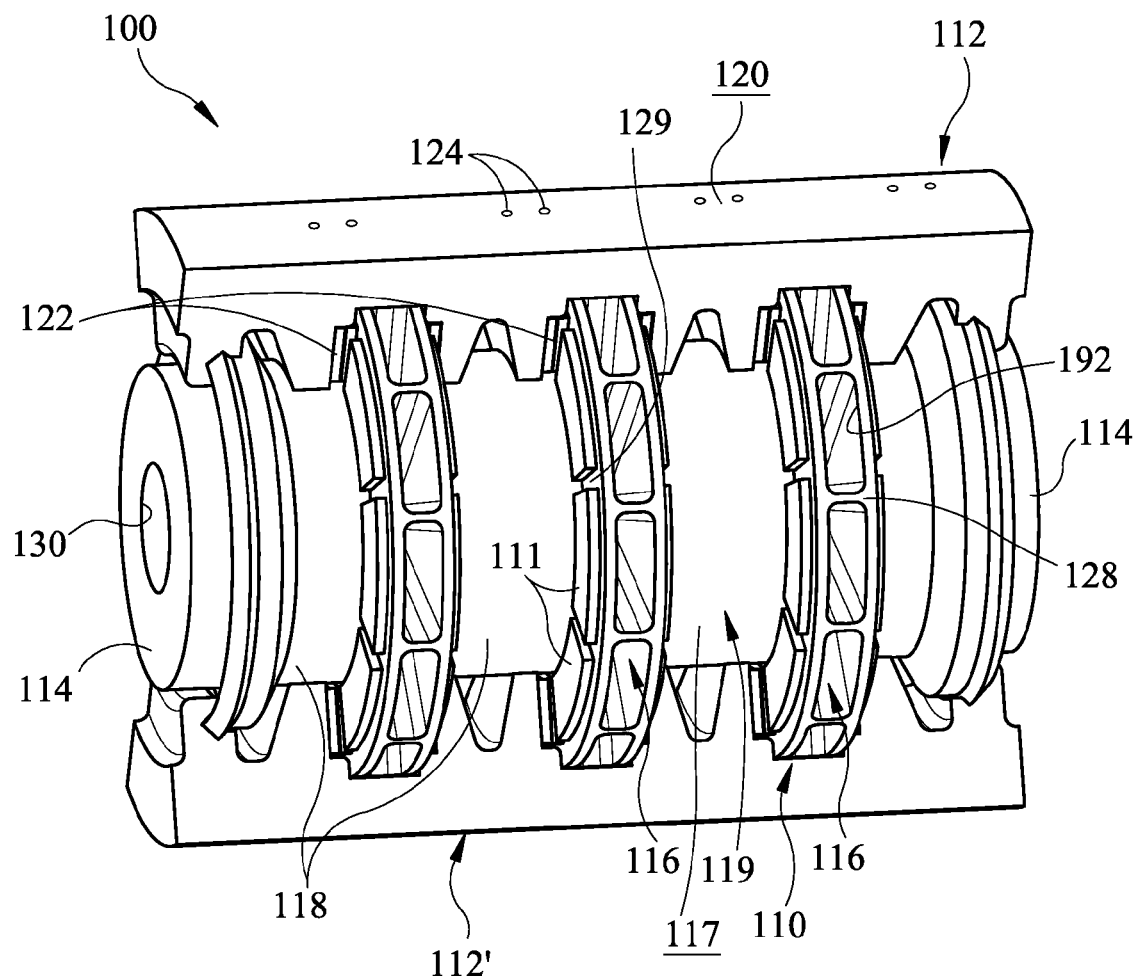
FIG. 8 is a perspective view of another apparatus according to one non-limiting embodiment.

In one embodiment, referring to FIGS. 1, 3, and 8, for example, the apparatus 100 can move the one or more carrier members 112 and/or 112' using the linear motor 110 and/or other suitable linear motors. In such an embodiment, each carrier member 112 and 112' may be provided with the permanent magnets 122 such that each carrier member 112 and 112' can be independently driven by the linear motor 110. The linear motor 110 can move the carrier members 112 and 112' owing to the magnetic interaction between the permanent magnets 122 on the carrier members 112 and 112' and the electromagnets 111 on the projections 128. By providing independent control of the carrier member 112 and 112', the carrier member 112 can be accelerated, decelerated, and/or moved independent of the carrier member 112', for example. Of course, the carrier member 112 will usually not be moved about the track such that it collides with the carrier member 112', although, in some embodiment, the carrier member 112 may lightly contact the carrier member 112' at various portions along the track 118.

The use of linear motor technology can provide substantial advantages over the related article transfer systems. Some article transfer systems can employ chains, sprockets, belts, racks, gears, lead screws, etc., none of which conveniently lend themselves to independent control of each linear motor and/or each carrier member 112.

Figure 6:
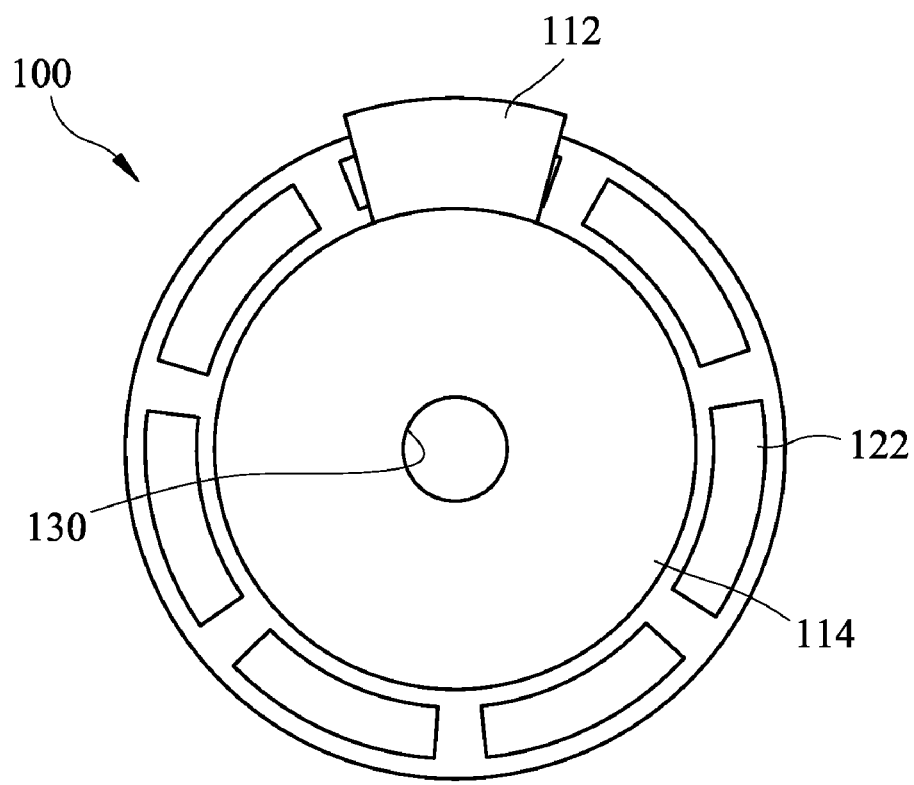
FIG. 6 is a side view of a carrier member mounted on an apparatus of FIG. 3 according to one non-limiting embodiment.
Figure 7:
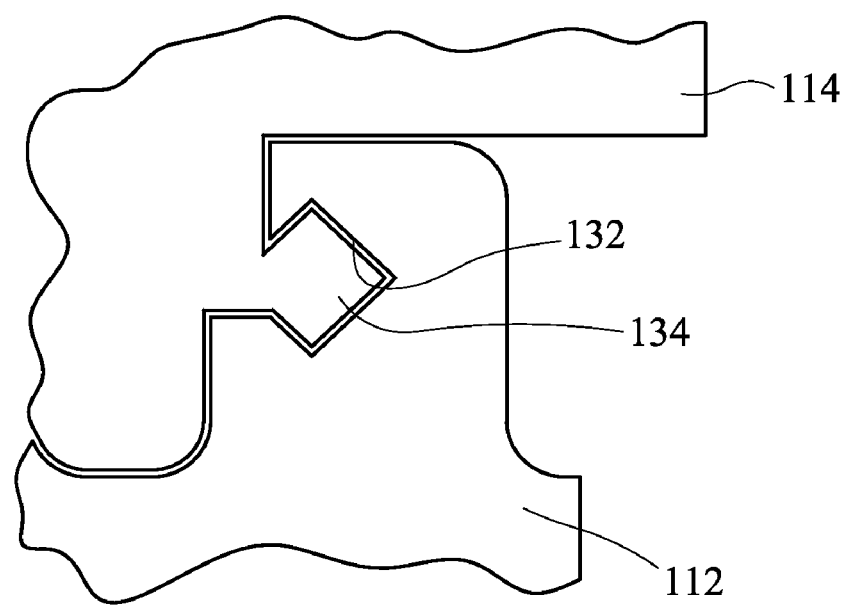
FIG. 7 is a view of a portion of a mounting structure of the apparatus of FIG. 3 according to one non-limiting embodiment.

In one embodiment, referring to FIGS. 5-7, a carrier member, such as the carrier member 112, for example, may be engaged with the support member 114 using one or more lips 134 (see e.g., FIG. 12 for one example of the lips) formed near end walls of the support member 114 and one or more recesses 132 formed near end walls of the carrier member 112. In various embodiments, the lips 134 and the recesses 132 may be formed at various locations along the length of an interface between the support member 114 and the carrier member 112, for example. In the endless track embodiment, the recesses 132 can extend fully around the endless track 118. In such an embodiment, the lips 134 may be configured to be slidably or movably engaged with the recesses 132 as the carrier member 112 moves relative to the endless track 118. Of course, surfaces of the lips 134 that engage surfaces of the recesses 132 and/or the surfaces of the recesses 132 can be low-friction surfaces, for example, to allow the carrier member 112 to easily travel about the track 118. In other embodiments, a lubricant can be provided intermediate the lips 134 and the recesses 132, for example.

In one embodiment, carrier members can be engaged with the support member using magnetic forces alone. In such an embodiment, magnets on the carrier members can be magnetically engaged with magnets on the projections of the support member to retain the carrier members within a rotational path about the track. In one embodiment, the magnets can be permanents magnets and/or electromagnets.

In one embodiment, referring to FIG. 1, the first carrier 105 may transfer the articles 102, at a rate of 1,000 articles 102 per minute, with a pitch of the articles 102 being about 4 inches, to the carrier web 103 on the second carrier 106, traveling at a rate of 1,000 finished products per minute, with a pitch of the finished products being about 17 inches. As a result, the speed of the first carrier 105 may be slower than the speed of the second carrier 106, for example, such that the articles 102 can be properly placed on the carrier web 103 by the apparatus 100. This arrangement may require the carrier member 112 to accelerate for at least a portion of the time, from when the carrier member 112 receives the articles 102 in the receiving zone 10 to when the carrier member 112 deposits the articles 102 onto the carrier web 103 on the second carrier 106 in the application zone 12, to match the faster speed of the second carrier 106. As discussed above, the use of the linear motor technology allows for such acceleration (or allows for deceleration, for example). In one embodiment, the speed of the first carrier 105 may be faster than the speed of the second carrier 106 to properly place the articles 102 onto the carrier web 103. In such an embodiment, the carrier member 112 may be required to decelerate at least part of the time, from when the carrier member 112 receives the articles in the receiving zone 10 to the time the carrier member 112 deposits the articles 102 on the second carrier 106 in the application zone 12, to match the slower speed of the second carrier 106.

In various embodiments, referring to FIGS. 1-3, the outer surface 120 of the carrier member 112 may travel along and define an orbital path about the track 118 of the support member 114 when moved by the linear motor 110. The orbital path passes through the receiving zone 10 and the application zone 12 when receiving the articles 102 from the first carrier 105 and when applying the articles 102 to the carrier web 103, respectively. Stated another way, the receiving zone 10 and the application zone 12 may be defined by particular regions of the orbital path where the articles 102 are transferred. In various embodiments, the receiving zone 10 and the application zone 12 may be at other locations about the orbital path depending on the arrangement of the first carrier 105 relative to the second carrier 106, for example.

As discussed above, now referring to FIG. 8, the apparatus 100 may comprise at least a second carrier member 112'. The second carrier member 112' may be movably engaged with the support member 114 and configured to move about or relative to the track 118 in the same or substantially the same manner as the one or more carrier members described above. The use of two carrier members 112 and 112' may allow for some flexibility in the manufacturing process. For example, the first carrier member 112 and the second carrier member 112' may work together to transfer the articles 102 from the first carrier 105 to the second carrier 106. The first carrier 112 may be depositing the articles 102 in the application zone 12 onto the carrier web 103 while the second carrier 112' is receiving the articles 102 in the receiving zone 10 from the first carrier 105. As such, by providing a second carrier member, more articles can be transferred from the first carrier 105 to the second carrier 106 in a given period of time. The use of the two carrier members 112 and 112' may further reduce the inertia of the system as the speed each of the carrier members 112 and 112' traveling relative to the track 118 can be reduced.

In one embodiment, the support member 114 and the carrier member 112 may be operably engaged with or configured to be operably engaged with each other via the various magnets of the linear motor 110. In one embodiment, referring to FIGS. 1 and 2, the first carrier 105 may be moving the articles 102 at a first speed, and the second carrier 106 may be moving the carrier web 103 at a second speed. The first speed may be in the range of 200 feet per minute to 400 feet per minute, and the second speed may be in the range of 850 feet per minute to 1700 feet per minute, for example. In one embodiment, the one or more linear motors 110 may be configured to move at least the outer surface 120 of the carrier member 112 at a third speed through the receiving zone 10 and at a fourth speed through the application zone 12. The third speed may be different than, slower than, or faster than the fourth speed. In one embodiment, the third speed may be equal to, or substantially equal to, or different than the first speed, and the fourth speed may be equal to, or substantially equal to, or different than the second speed. The third speed may be in the range of 85 to 115% of the first speed and, similarly, the fourth speed may be in the range of 85 to 115% of the second speed, for example. In one embodiment, the third speed may be in the range of 170 feet per minute to 460 feet per minute, and the fourth speed may be in the range of 725 feet per minute to 1950 feet per minute, for example.

It is to be appreciated that while linear motor technology is contemplated to carry out the objectives of the apparatus 100, the structure, form and/or control of the linear motors can vary based on particular applications of the apparatus 100. As such, any suitable linear motor system can be used to accomplish the objectives of the apparatuses consistent with the present disclosure. Information concerning linear motor technology is generally available. In one embodiment, more than one linear motor may be used to sufficiently accelerate and/or decelerate one or more carrier members relative to a track. In one non-limiting example embodiment, referring to FIG. 3, three linear motors 110 can be used. In other various embodiments, one, two, four, five, six etc. linear motors can be used.

It will be appreciated that any linear motor control system and associated sensors can be provided to indicate the position, velocity, and/or acceleration of one or more carrier members about the track. In one embodiment, the support member 114 may be provided with an encoder track configured to operably interact with one or more encoders or other sensors to sense the position of the carrier members 112 and 112' about the track 118, for example. In such an embodiment, the control system can receive one or more signals from the sensors or the encoders and register and synchronize each carrier member 112 and 112' being driven by the one or more linear motors with the first carrier 105 and the second carrier 106 to carry out appropriate placement of the articles 102 on the carrier web 103 on the second carrier 106. In one embodiment, the carrier member 112 can be driven and controlled independently of the carrier member 112', for example. Thus, the carrier members 112 and 112' traveling about the track 118 may be registered or indexed, and synchronized in position, velocity, and/or acceleration with the first carrier 105, the second carrier 106, and/or each other. The linear motor control system may allow the carrier members 112 and 112' to receive the articles 102 from the first carrier 105 and to deposit the articles 102 on the carrier web 103 traveling on the second carrier 106, when the articles 102 on the first carrier 105 are traveling at a speed different than the speed of the carrier web 103. For example, the carrier members 112 and 112' may be synchronized in position and time with the first carrier 105 and the second carrier 106 using the one or more linear motors 110 to drive the carrier member 112 and 112' at a third speed while receiving the articles 102 from the first carrier 105 and then accelerating and/or decelerating the carrier members 112 and 112' to a fourth speed while depositing the articles 102 on the carrier web 103. Given the position of the first carrier member 112, the linear motor 110 and its control system can synchronize the second carrier member 112' with the first carrier 105, the second carrier 106, and/or the first carrier member 112, for example.

As mentioned above, one advantage of the linear motor technology of the present disclosure is the reduction of system inertia. Since each carrier member is independent, the inertia of the system is only that of an individual carrier member and an article that is being transported by the individual carrier member. In related article transfer systems, the carrier members are generally interconnected through a transmission, for example. The interconnection and the addition of the transmission may substantially increase the system inertia of the related systems. The lower inertia provided through the use of the linear motor configuration of the present disclosure may provide for greater efficiency in transferring articles 102 from the first carrier 105 to the second carrier 106, for example.

In various embodiments, any suitable linear motor systems can be used with the apparatuses of the present disclosure. Such linear motor systems can be provided with any form of suitable control that is operable to drive and synchronize the individual carrier members of the system in a zone, section, and/or segment of the track 118, for example. In one linear motor system, micro-controllers for various zones may be networked with a controller to not only provide the linear motor system with high position accuracy, but also to control individual carrier members, for example.

In one embodiment, referring to FIG. 3, the electromagnets 111 may face a negative magnetic pole or a positive magnetic pole of the permanent magnets 122 such that the electromagnets 111 can either attract or repel the permanent magnets 122 to move the carrier member 112 about the track 118 when the electromagnets 111 are energized. In such an embodiment, an electrical current can always be run through coils of the electromagnets 111 in the same direction to produce the same magnetic field. In other embodiments, the electromagnets 111 can always face one magnetic pole of the permanents magnets 122 and the electrical current can be run through the coils of the electromagnets 122 in different directions to change the magnetic field produced by the electromagnets 122 and, thereby, attract or repel the permanent magnets 122 based on which way the electrical current is run through the coils (e.g., Right Hand Rule). This attraction or repulsion can move the carrier member 112 about the track 118 in any suitable direction. It can be appreciated that any suitable electromagnet configurations can be used with the present disclosure.

In some instances, the electrical current provided to the electromagnets 111 may generate a significant amount of heat in the electromagnets 111. The heat generated in the electromagnets 111 may cause portions of the apparatuses, the articles 102, the carrier web 103, the first carrier 105, the second carrier, and/or any other component of the manufacturing system to become hot and/or to deform. In one embodiment, referring to FIGS. 3, 4, and 8, the one or more conduits 131 of the vacuum manifold 116 may be positioned within portions of the projections 128 and proximate to the electromagnets 111, such that the vacuum manifold 116 may be configured to dissipate heat from the electromagnets 111, as air is drawn into the one or more conduits 131 through openings 192, for example. In such as embodiment, the heat can be dissipated from the electromagnets 111 to reduce the temperature of the electromagnets 111 and prevent, or at least minimize, heat damage to components of the system and/or to the articles 102, for example. Other known methods for dissipating heat from electromagnets may also be used, such as by providing a cooling system comprising glycol, for example, for cooling the electromagnets.

Additional details regarding linear motors can be found in U.S. Pat. No. 7,134,258, issued on Nov. 14, 2006, and entitled "Packaging Apparatus and Methods" to Kalany et al., and U.S. Pat. No. 6,876,107, issued on Apr. 5, 2005, and entitled "Controlled Motion System" to Jacobs, both of which are hereby incorporated by reference in their entirety.

Figure 9:
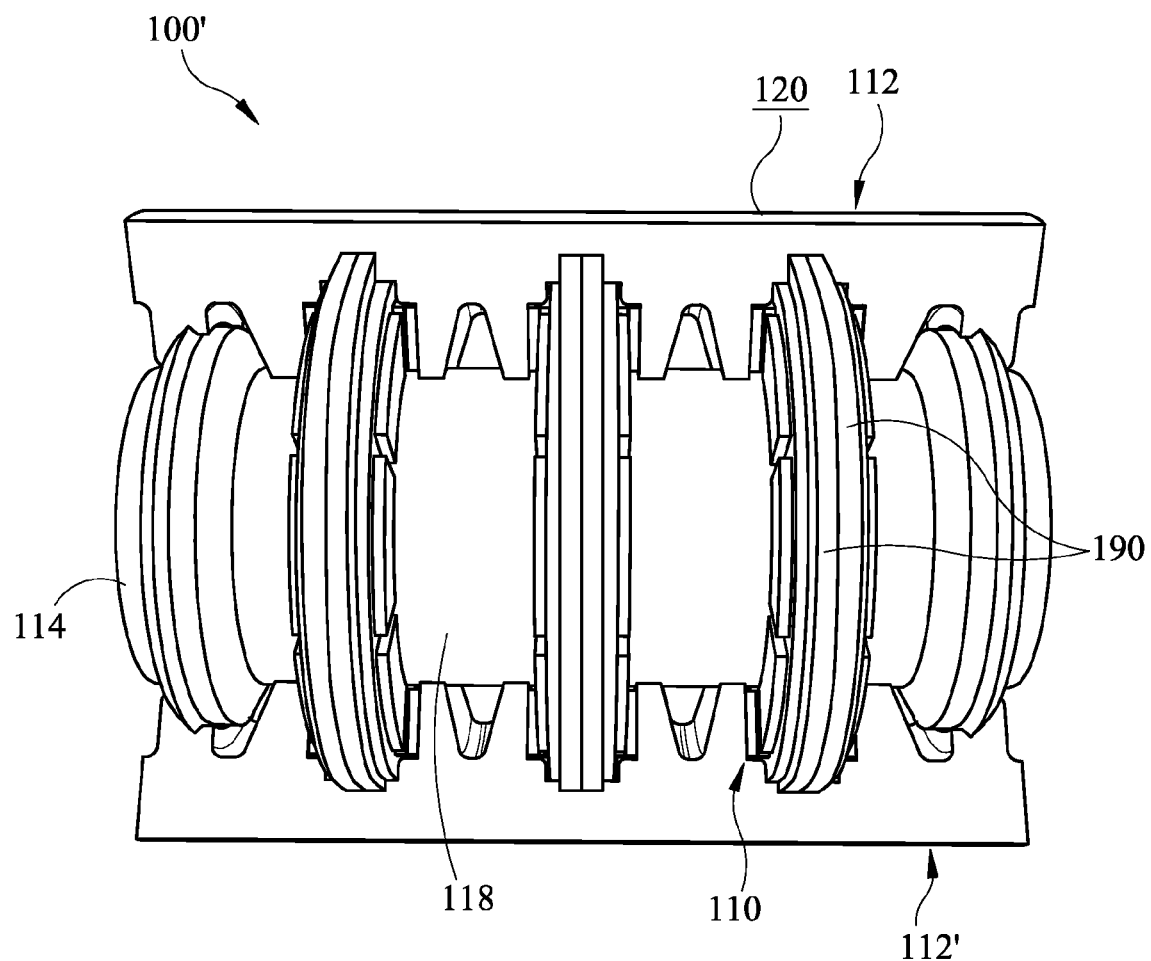
FIG. 9 is a perspective view of an apparatus comprising a sealing system according to one non-limiting embodiment.
Figure 10:
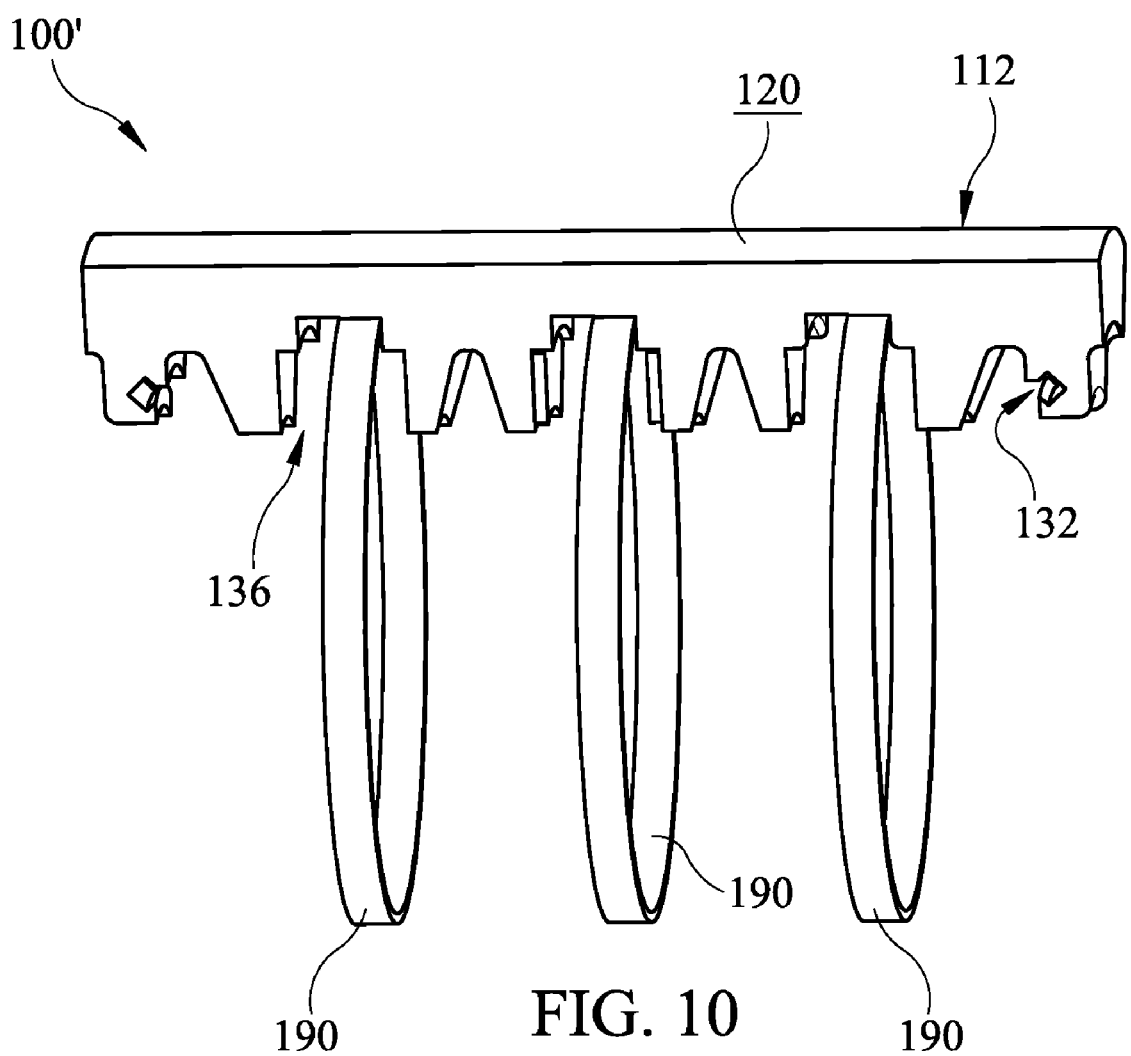
FIG. 10 is a perspective view of one of the carrier members of the apparatus of FIG. 9 according to one non-limiting embodiment.

In one embodiment, referring to FIGS. 9 and 10, an apparatus 100' can comprise one or more bands 190 attached to or formed with the carrier members 112 and 112' for sealing the openings 192 in the projections 128 of the vacuum manifold 116 that are not positioned under the carrier members 112 and 112'. The one or more bands 190 may be configured to move with the carrier members 112 and 112' as the carrier members 112 and 112' move about the track 118. Stated another way, the bands 190 can rotate relative to the projections 128 as the carrier members 112 and 112' move about the track 118. In one embodiment, the bands 190 may each comprise a first end attached to a first region of the carrier members 112 and 112' and a second end attached to a second region of the carrier members 112 and 112'. A gap can be formed on the carrier members 112 and 112' intermediate the first end and the second end of the bands 190 such that the vacuum can be provided to the carrier members 112 and 112' through the gap. In other embodiments, the band can form an enclosed shape, such as a circle for example. In such an embodiment, a hole can be formed in the bands 190 proximate to where the bands 190 are attached to the carrier members 112 and 112'. The hole can allow the vacuum from one or more conduits 131 to enter the carrier members 112 and 112' much like the gap discussed above. The bands 190 can seal the openings 192 that are not engaged with the carrier members 112 and 112'. As such, the bands 190 can seal most of the openings 192 and, thus, a sufficient vacuum can be created within the carrier members 112 and 112' to hold the articles 102 in place on the outer surface 120 of the carrier members 112 and 112'. In various embodiments, each carrier member 112 and 112' can comprise three or more bands 190 configured to engage three or more projections 128 on the support member 114. Generally speaking, a band can be provided on each carrier member for each projection of a support member. In one embodiment, the bands 190 can be comprised of a light weight, low friction material, such as titanium or aluminum, for example. In various embodiments, the low weight, low friction material of the bands 190 may be coated with a material such as polytetrafluoroethylene (PTFE) and/or any other suitable low friction material used for reducing the coefficient of friction between moving parts.

In one embodiment, each of the bands 190 may form an arcuate inner perimeter configured to engage an arcuate outer perimeter of the projections 128 to seal, or at least partially seal, the openings 192, which are free from engagement with the carrier members 112 and 112', from the surrounding atmosphere. In other embodiments, the bands 190 can form a circular inner perimeter or a partially circular inner perimeter to fit over a circular outer perimeter, or a partially circular outer perimeter, of the projections 128. In various embodiments, the bands 190 may at least partially cover the openings 192, which are not being covered by the carrier members 112 and 112', as the carrier members 112 and 112' rotate about the track 118. The openings 192 covered by the carrier members 112 and 112' may be in fluid communication with the carrier members 112 and 112' through the opening or the gap in the bands 190, as discussed above. When more than one carrier member is used in the apparatus, the bands 190 may be attached to or integrally formed with each of the carrier members, as illustrated with respect to one carrier member 112 in FIG. 10. In such an arrangement, the bands 190 may each seal a relative area of the openings 192 in the vacuum manifold 116 and a first band of a first carrier member 112 can move relative to a second band of a second carrier member 112' as the first and second carrier members 112 and 112' are moved about the track 118. In such an embodiment, if two the carrier members 112 and 112' are used, two bands 190 may substantially cover the appropriate openings 192. Therefore, each of the two bands 190 can seal approximately 50% of the area of the appropriate openings 192 in each projection 128 (see, e.g., FIG. 9). If three carrier members are used, three bands for each projection 128 may substantially cover the appropriate openings 192 in each projection 128. Therefore, each of the bands 190 may seal approximately 33% of the area of the appropriate openings 192 of each projection 128. As illustrated, when more than one band is used, a first band can be positioned beside or adjacent to a second band, such that the overall width of the two bands is large enough to cover the width of the openings 192. In such an embodiment, the first band can be sealed to the second band, in a movable fashion, to prevent or at least inhibit air being drawn into the openings 192 intermediate the first and second bands.

In one embodiment, the vacuum system may control the amount of vacuum pressure provided to the conduits 131 and the passages 126 using one or more valves, which may control the amount of vacuum pressure applied to the carrier members 112 and 112' and ultimately to the apertures 124. In one embodiment, as a carrier member 112 moves over a particular opening 192, the valve controlling the vacuum pressure provided to that particular opening 192 may be opened, thereby allowing the vacuum pressure from the vacuum manifold 116 to extend into the carrier member 112. In such an embodiment, the one or more valves controlling the vacuum to the other openings 192 not under the carrier member 112 may be closed to prevent, or at least inhibit, the vacuum system from drawing air into the other openings 192.

In one embodiment, the vacuum system may control the amount of vacuum pressure provided to the conduits 131 and the passages 126 using an inner sleeve which may be provided within the bore 130 of the support member 114. In one embodiment, as a carrier member moves over a particular opening 192, an opening in the inner sleeve may be configured to move with the carrier member 112 under the same opening 192, thereby allowing the vacuum pressure from the vacuum manifold 116 to extend into the carrier member 112. In such an embodiment, a portion of the inner sleeve controlling the vacuum to the other openings 192 not under the carrier member, for example, the solid portion of the inner sleeve, may be configured to prevent, or at least inhibit, the vacuum pressure drawing air into the other openings 192. The inner sleeve may comprise a rubbing seal or a no contact seal.

Figure 11:
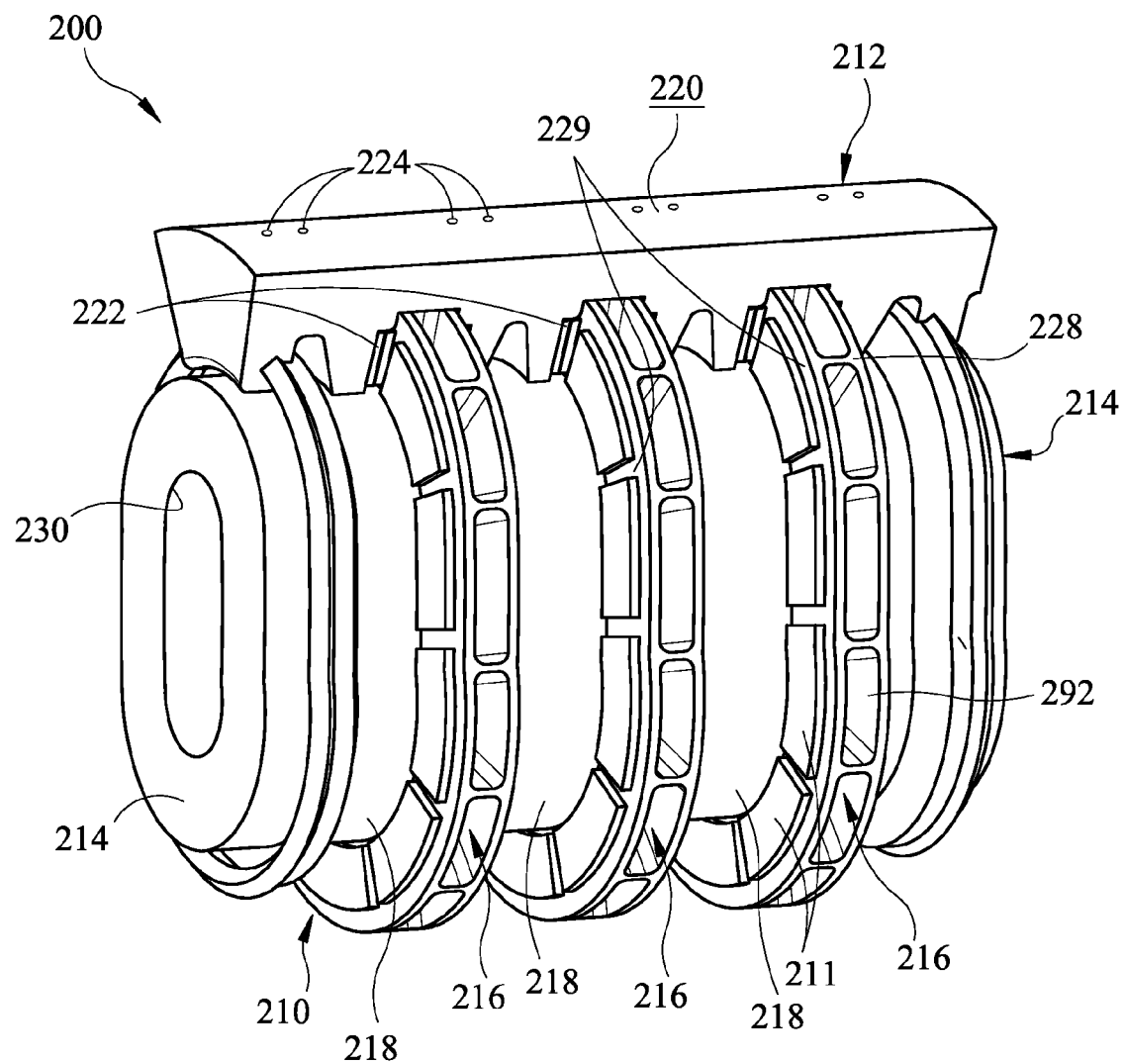
FIG. 11 is a perspective view of yet another apparatus according to one non-limiting embodiment.

In one embodiment, referring to FIG. 11, a track 218 and/or a support member 214 of an apparatus 200 may define a substantially elliptical or ovate perimeter and/or may comprise one or more arcuate portions. In other embodiments, the track 218 may define any other suitably shaped perimeter, such as an arcuate perimeter, and/or a circular perimeter, for example. The apparatus 200 may comprise one or more carrier members 212 movably engaged with the support member 214. The support member 214 may comprise at least one vacuum manifold 216. Unless otherwise indicated above, the components with corresponding reference numerals (e.g., 114, 214) can have the same or a similar structure and function as discussed above with respect to other embodiments. As such, these components will not be discussed in detail again, with respect to the apparatus 200, for the sake of brevity.

Figure 12:
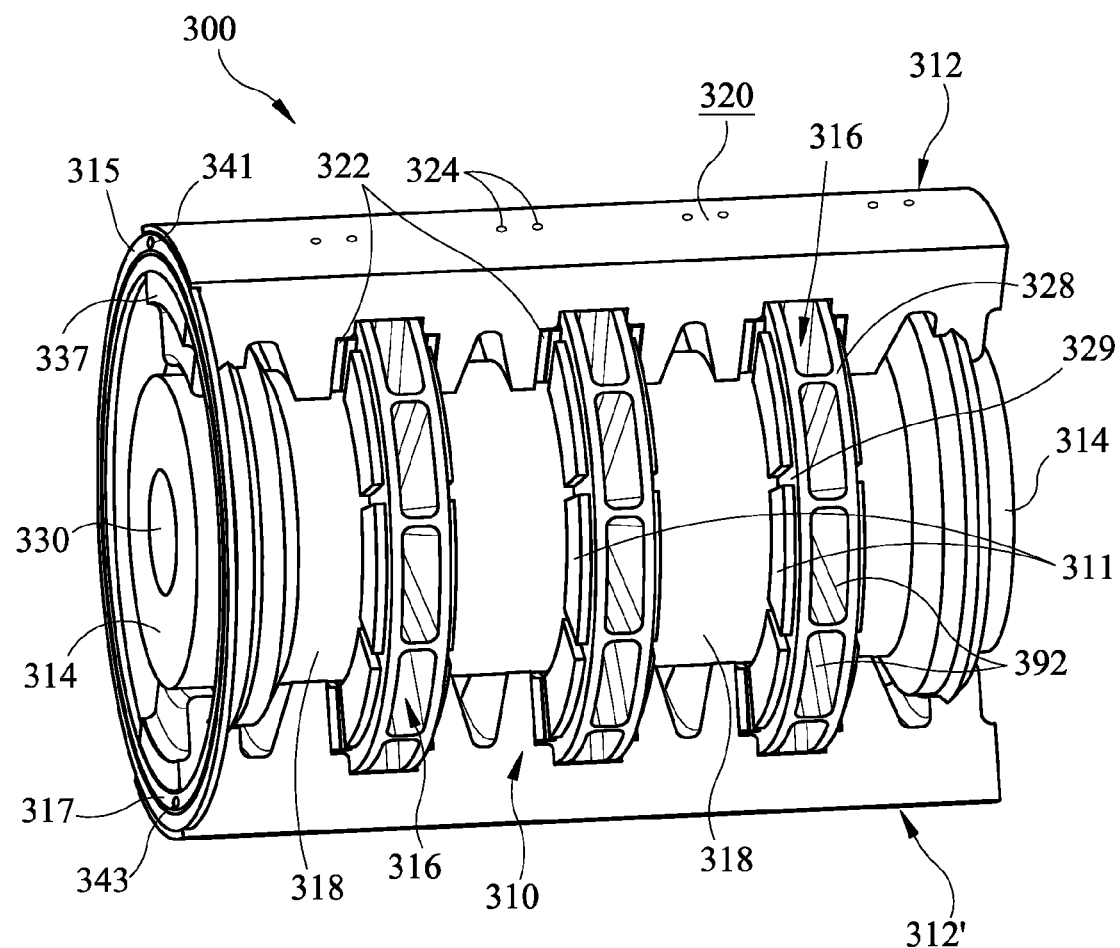
FIG. 12 is a perspective view of another apparatus according to one non-limiting embodiment.

In one embodiment, referring to FIG. 12, an apparatus 300 may employ an alternate vacuum system arrangement in addition to or in lieu of the vacuum systems and vacuum manifolds discussed above. The apparatus 300 may comprise a vacuum manifold 315 positioned proximate to an end of a support member 314. In addition, the vacuum manifold 315 may be positioned proximate to a side wall 337 of carrier members 312 and 312'. The vacuum manifold 315 may be in fluid communication with the carrier member 312, such that a vacuum can be provided to the carrier member 312, through a passage (not illustrated) in the carrier member 312, and ultimately to apertures 324. In one embodiment, the vacuum manifold 315 may be configured to be fixed and the carrier member 312 may be configured to be moved relative to the vacuum manifold 315, as the carrier member 312 moves relative to the track 318.

Figure 13:
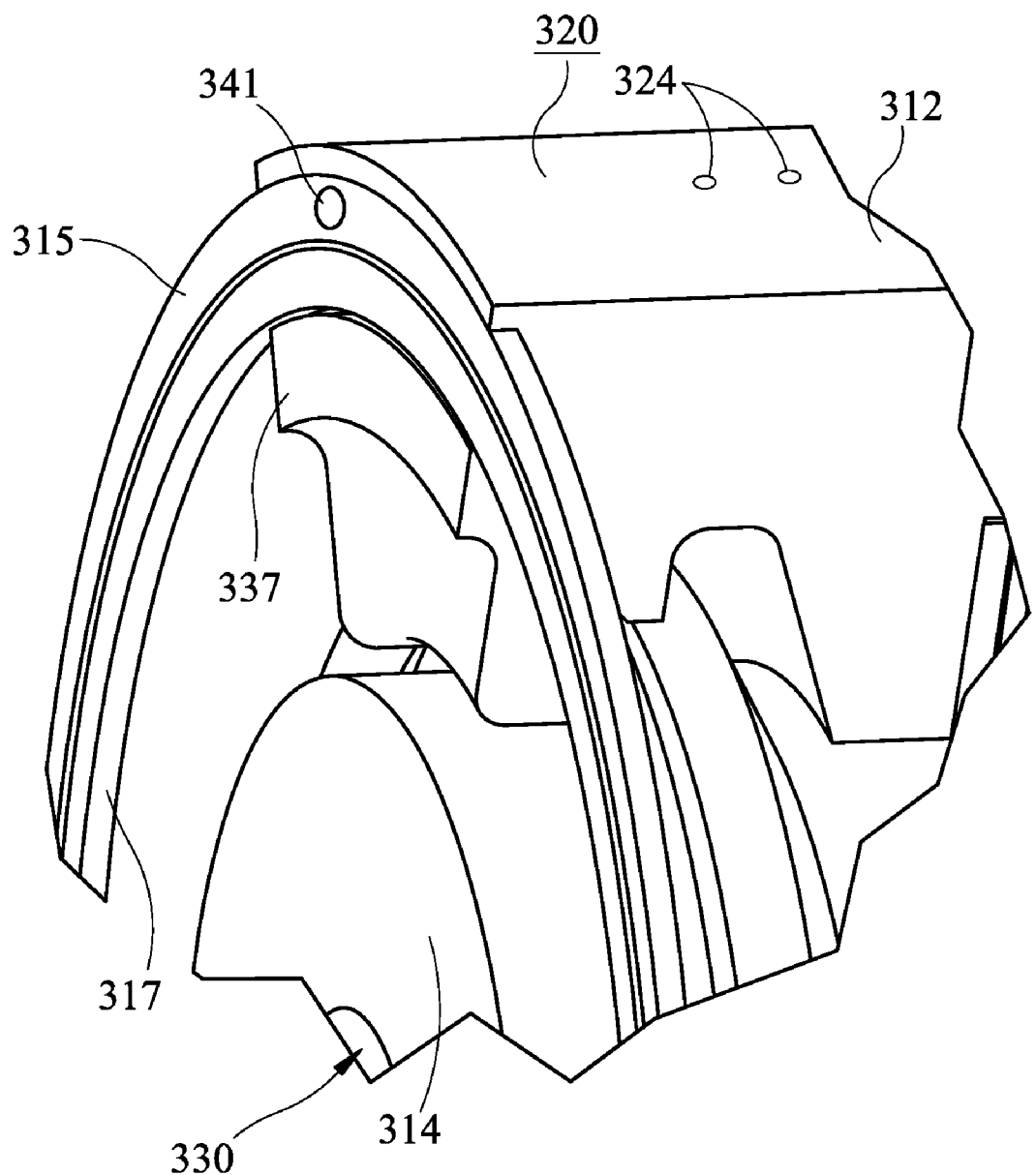
FIG. 13 is a view of a portion of the apparatus of FIG. 12 according to one non-limiting embodiment.
Figure 14:
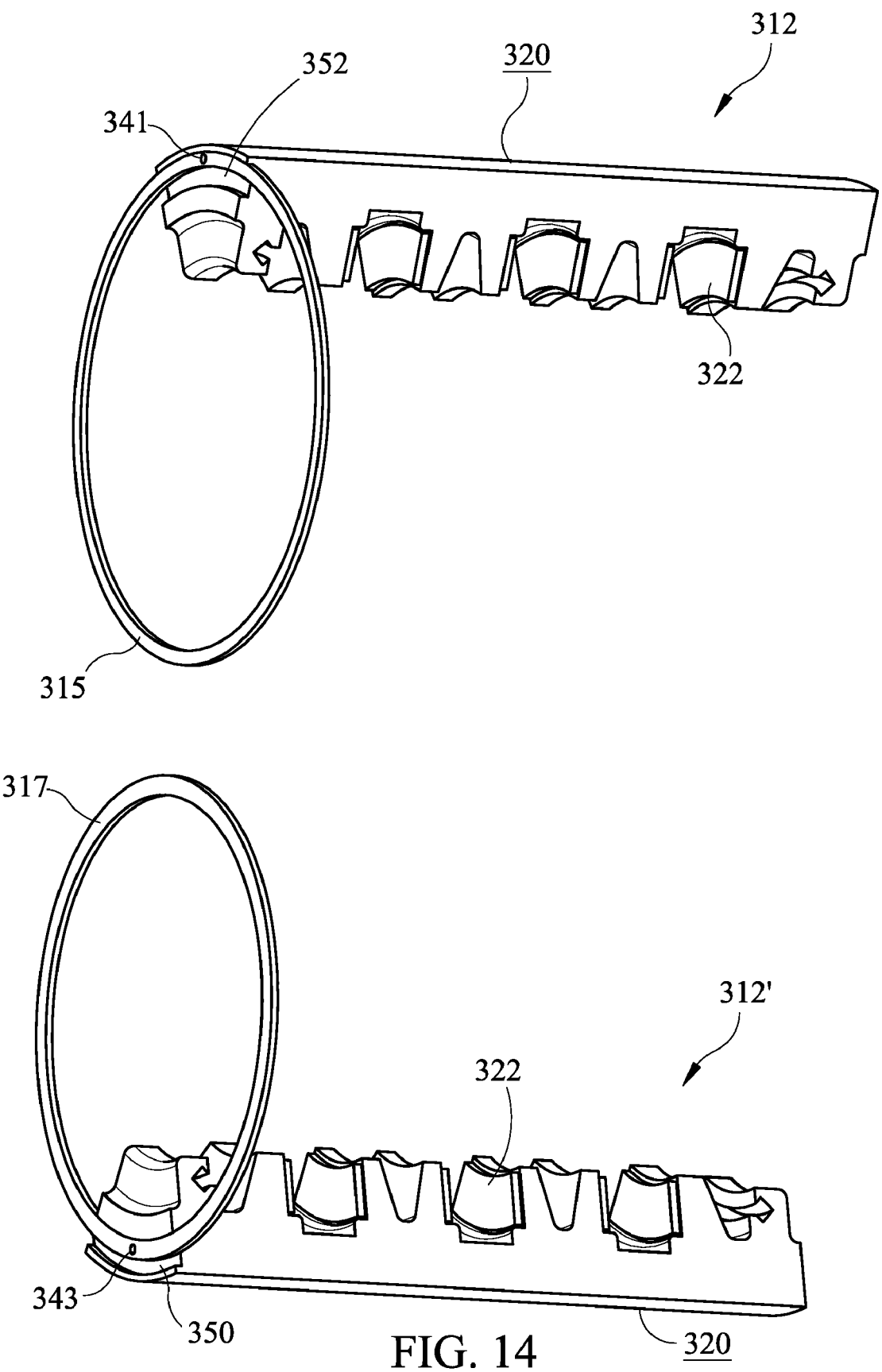
FIG. 14 is a perspective view of the carrier members of the apparatus of FIG. 12 according to one non-limiting embodiment.

In one embodiment, referring to FIGS. 12-14, two carrier members 312 and 312' may be used with the apparatus 300, for example. Each carrier member 312 and 312' can be associated with a vacuum manifold 315 and 317, respectively. The vacuum manifold 317 can interact with the carrier member 312', similar to or the same as how the vacuum manifold 315 interacts with the carrier member 312. The vacuum manifolds 315 and 317 may be configured to be retained within recesses 350 and 352, respectively, formed in both of the carrier members 312 and 312'. The recesses 350 and 352 may allow the carrier members 312 and 312' to move relative to the vacuum manifolds 315 and 317, as the carrier members 312 and 312' move relative to the track 318. The first vacuum manifold 315 may have a larger diameter or perimeter than a diameter or a perimeter of the second vacuum manifold 317 to allow the second manifold 317 to be configured to be positioned at least partially within the inner diameter or perimeter of the first vacuum manifold 315 (see, e.g., FIG. 13).

In one embodiment, the vacuum manifolds 315 and 317 may be in fluid communication with a vacuum system at inlet ports 341 and 343, respectively. The vacuum system can comprise any system capable of providing a vacuum to the vacuum manifolds 315 and 317 to allow a vacuum to be provided to the carrier members 312 and 312' and ultimately to the apertures 324 in each of the carrier members 312 and 312'.

In one embodiment, at least one of the vacuum manifolds 315 and 317 can be used in conjunction with the vacuum manifolds 116 or 216 described above. In such an embodiment, the vacuum manifolds 315 and 317 can be used to provide a vacuum to the one or more carrier members 312 and 312' and the vacuum manifolds 116 or 216 can be used to cool electromagnets 311 of the one or more linear motors 310. In one embodiment, instead of providing a vacuum to the vacuum manifold 316, a positive pressure can be provided to the vacuum manifold 316 by a pump or other suitable device. In such an embodiment, air can be blown out of the openings 392 in the projections 328 to dissipate heat from the electromagnets 311. Stated another way, the air flow being forced from the openings 392 of the projections 328 can absorb heat from the electromagnets 111 to cool the electromagnets 111.

Figure 15:
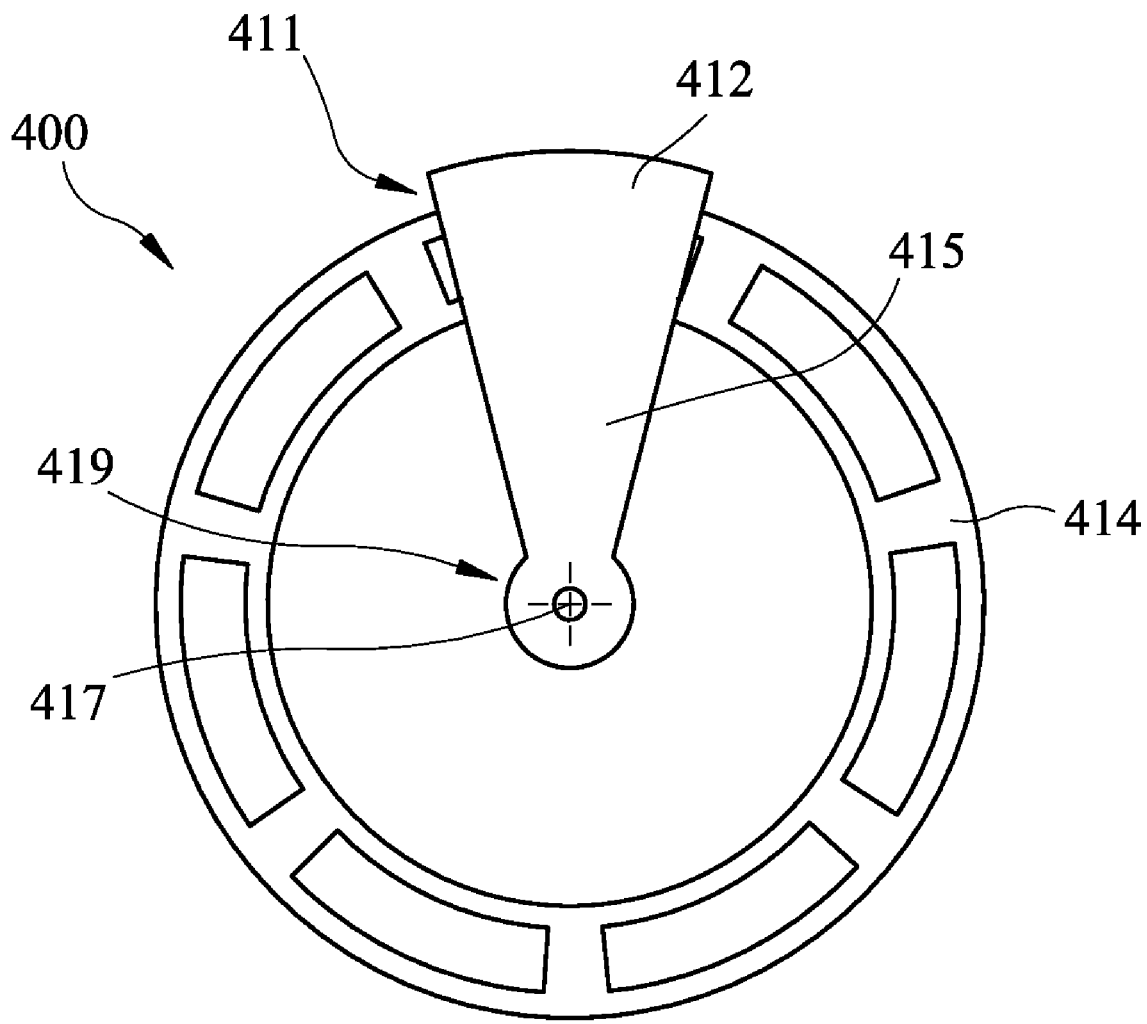
FIG. 15 is a side view of a mounting structure for a carrier member of an apparatus according to one non-limiting embodiment.

In one embodiment, referring to FIG. 15, a carrier member 412 may be mounted to or formed with a rotatable arm 415. The rotatable arm can 415 be attached to the support member 414 at a point along or proximate to a longitudinal axis 417 of the support member 414. In one embodiment, the rotatable arm 415 may be attached to or formed with the carrier member 412 at a first end 411 and attached to the support member 414 at a second end 419. The rotatable arm 415 can rotate about the longitudinal axis 417 as the carrier member 412 rotates about the support member 414 and/or moves relative to a track of the support member 414.

In one embodiment, a method of transferring an article from a first carrier moving at a first speed to a second carrier moving at a second speed is provided. The method can comprise providing a support member which can comprise an endless track or a track. The endless track can comprise an arcuate perimeter or another suitable perimeter, as discussed above. The method can also comprise providing a carrier member movable relative to the support member. The carrier member can comprise an outer surface and at least one aperture in the outer surface. The aperture can be in fluid communication with a vacuum manifold. The method can further comprise receiving an article from the first carrier onto the outer surface of the carrier member, and holding the article on the outer surface of the carrier member with air passing through the aperture to the vacuum manifold. The carrier member can be moved using a linear motor such that it can move relative to the support member about the endless track to a position proximate to the second carrier. The linear motor can comprise at least one permanent magnet on the carrier member and at least one electromagnet on the support member. The at least one electromagnet can be cooled by air being drawn into the vacuum manifold through an opening in the support member, for example. The article can then be deposited onto the second carrier by the carrier member. The liner motor can move the carrier member at a third speed when receiving the article from the first carrier and can move the carrier member at a fourth speed that is different than the third speed when depositing the article onto the second carrier.

Although various embodiments have been described herein, many modifications and variations to those embodiments may be implemented. For example, different types of carrier members and/or support members may be employed. In addition, combinations of the described embodiments may be used. Also, where materials are disclosed for certain components, other materials may be used. The foregoing description and following claims are intended to cover all such modification and variations.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for transferring one or more articles from a first carrier moving at a first speed to a second carrier moving at a second speed that is different than the first speed, the apparatus comprising:
    a support member comprising
        a vacuum manifold, and
        an endless track defining an arcuate perimeter;
    a carrier member movably engaged with the support member and movable with respect to the endless track, the carrier member comprising
        an outer surface configured to receive the one or more articles from the first carrier in a receiving zone and configured to deposit the one or more articles onto the second carrier in an application zone,
        an aperture in the outer surface, and
        a channel in fluid communication with the aperture and configured to be in fluid communication with the vacuum manifold; and
    a linear motor positioned at least on the support member, wherein the linear motor is operably engaged with the carrier member and is configured to move the carrier member relative to the endless track, wherein the linear motor is configured to move the outer surface of the carrier member at a third speed through the receiving zone and at a fourth speed through the application zone, and wherein the third speed is different than the fourth speed.

2. The apparatus of claim 1, wherein the linear motor comprises an electromagnet positioned on the support member.

3. The apparatus of claim 2, wherein the linear motor comprises a permanent magnet positioned on the carrier member.

4. The apparatus of claim 1, comprising a second carrier member movably engaged with the support member and movable with respect to the endless track.

5. The apparatus of claim 1, comprising a rotatable arm, wherein the rotatable arm is attached to the carrier member at a first end and is attached to the support member at a second end, and wherein the rotatable arm is configured to rotate about a longitudinal axis of the support member upon movement of the carrier member.

6. The apparatus of claim 1, wherein the vacuum manifold comprises a projection extending outwardly from the endless track.

7. The apparatus of claim 6, wherein the carrier member comprises a receiving slot, wherein the linear motor comprises a permanent magnet, wherein the receiving slot is configured to receive the projection, and wherein the permanent magnet is at least partially positioned within the receiving slot.

8. The apparatus of claim 7, wherein the linear motor comprises an electromagnet positioned on the support member, wherein the electromagnet is configured to be magnetically engaged with the permanent magnet, and wherein the carrier member defines a recess configured to be engaged with a lip extending from the support member.

9. The apparatus of claim 1, wherein the support member defines an axially extending bore therein, and wherein the axially extending bore comprises a portion of the vacuum manifold.

10. The apparatus of claim 1, comprising a second vacuum manifold positioned proximate to an end wall of the support member, wherein the second vacuum manifold is in fluid communication with the aperture in the carrier member, and wherein the linear motor is configured to move the carrier member relative to the second vacuum manifold.

11. The apparatus of claim 1, wherein the endless track comprises a substantially circular track.

12. The apparatus of claim 1, wherein the vacuum manifold is in fluid communication with the channel of the carrier member at a location intermediate the vacuum manifold and the carrier member.

13. An apparatus for transferring an article from a first carrier moving at a first speed to a second carrier moving at a second speed that is different than the first speed, the apparatus comprising:
    a support member comprising a track, wherein the track comprises an arcuate portion;
    a carrier member configured to be moved relative to the track, the carrier member comprising
        a surface configured to receive the article from the first carrier in a receiving zone and deposit the article onto the second carrier in an application zone,
        an aperture in the surface, and
        a passage in fluid communication with the aperture;
    a vacuum manifold in fluid communication with the passage, wherein the carrier member is configured to be moved relative to the vacuum manifold; and a linear motor operably engaged with the carrier member and configured to move the carrier member relative to the track, wherein the linear motor is configured to move the surface of the carrier member at a third speed through the receiving zone and at a fourth speed through the application zone, and wherein the third speed is different than the fourth speed.

14. The apparatus of claim 13, wherein the linear motor comprises an electromagnet positioned on the support member and a permanent magnet positioned on the carrier member.

15. The apparatus of claim 14, wherein the vacuum manifold comprises a projection extending radially outward from the track.

16. The apparatus of claim 14, wherein the vacuum manifold is positioned proximate to an end wall of the support member.

17. The apparatus of claim 14, wherein the vacuum manifold is positioned proximate to a portion of the linear motor such that the vacuum manifold is configured to dissipate heat from the electromagnet.

18. The apparatus of claim 14, wherein the vacuum manifold comprises a seal movable between a first, engaged position and a second, disengaged position, wherein the seal permits fluid communication between a portion of the vacuum manifold and the passage in the carrier member when in the second, disengaged position, and wherein the seal seals the portion of the vacuum manifold from the passage in the carrier member when in the first, engaged position.

19. A method of transferring an article from a first carrier moving at a first speed to a second carrier moving at a second speed, the method comprising the steps of:

providing a support member comprising an endless track, wherein the endless track comprises an arcuate perimeter;

providing a carrier member movable relative to the support member, the carrier member comprising an outer surface and an aperture in the outer surface, wherein the aperture is in fluid communication with a vacuum manifold;

receiving an article from the first carrier onto the outer surface of the carrier member;

holding the article on the outer surface of the carrier member with air passing through the aperture to the vacuum manifold;

moving the carrier member with a linear motor such that carrier member moves relative to the support member about the endless track to a position proximate to the second carrier, wherein the linear motor comprises a permanent magnet on the carrier member and an electromagnet on the support member;

cooling the electromagnet with air passing through the aperture to the vacuum manifold; and depositing the article from the carrier member onto the second carrier.

20. The method of claim 19, wherein the linear motor moves the carrier member at a third speed when receiving the article from the first carrier, and wherein the linear motor moves the carrier member at a fourth speed that is different than the third speed when depositing the article onto the second carrier.

* * * * *